United States Patent [19]

Wolfe et al.

[11] 4,183,931

[45] Jan. 15, 1980

[54] 2-KETOALKYL-4(3H)-QUINAZOLINONES

[75] Inventors: James F. Wolfe, Blacksburg, Va.;
Terry L. Rathman, Hershey, Pa.

[73] Assignee: Research Corporation, New York, N.Y.

[21] Appl. No.: 831,446

[22] Filed: Sep. 8, 1977

[51] Int. Cl.² ............... A61K 31/505; C07D 239/90; C07D 239/91
[52] U.S. Cl. .................. 424/251; 544/284; 544/287
[58] Field of Search ............ 260/251 QA, 256.4 Q; 424/251; 544/287

[56] References Cited

U.S. PATENT DOCUMENTS

| | | | |
|---|---|---|---|
| 2,668,112 | 2/1954 | de Cat et al. | 260/251 QA |
| 3,086,910 | 4/1963 | Shetty et al. | 424/251 |

OTHER PUBLICATIONS

Burger, *Medicinal Chemistry*, 3rd Ed., (1970), p. 1396.

*Primary Examiner*—Paul M. Coughlan, Jr.
*Attorney, Agent, or Firm*—Haight & Huard

[57] ABSTRACT

2-Ketoalkyl-4(3H)-quinazolinones of the formula

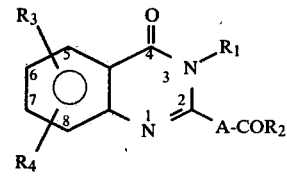

wherein
$R_1$ is an aliphatic, cycloaliphatic or hydrocarbon aromatic group of 1–10 carbon atoms;
A is divalent alkylene of 1 to 10 carbon atoms;
$R_2$ is an aliphatic, cycloaliphatic, hydrocarbon aromatic or heterocyclic group of 1–10 carbon atoms formed by condensing an acyl ester of the formula $R_2COOR'$ which can be dissociated to form $-COR_2$ and R'OH in which R' is the alcoholic portion of said ester; and
$R_3$ and $R_4$ are each hydrogen, hydroxy, amino, halogen, trifluoromethyl, alkyl, alkoxy, alkylthio or alkylsulfonyl each of 1-4 carbon atoms, the substituents other than hydrogen when present being preferably in the 6- and/or 7-position of the quinazolinone nucleus
provide compounds having useful activity as CNS depressants and anticonvulsants. A process is provided for preparing such compounds by ester condensation of a corresponding 2-alkyl-3-substituted-4(3H) quinazolinone with a condensable ester and excess sodium hydride in the presence of a strong ionization solvent such as refluxing 1,2-dimethoxyethane.

17 Claims, No Drawings

2-KETOALKYL-4(3H)-QUINAZOLINONES

BACKGROUND OF THE INVENTION

This invention was supported in part by Grant No. 10197 from the National Institutes of Health. In accordance with the terms thereof, this invention may be manufactured and used by the government of the United States of America for governmental purposes without the payment of any royalties thereon.

This invention relates to new 2-substituted-3-aryl-4(3H)-quinazolinones having useful pharmaceutical properties, methods for the preparation thereof, and methods and compositions for the use thereof.

Interest in derivatives of 4(3H)-quinazolinones as medicinal agents was stimulated by the elucidation of the structure of febrifugine in J.A.C.S. 72:3323 (1950). This compound is the active principle of the ancient antimalarial preparation Ch'ang Shan. Consequently, many synthetic derivatives of febrifugine as well as other compounds containing the 4(3H)-quinazolinone nucleus began appearing in the literature, e.g. see W. L. F. Armarego, "Fused Pyrimidines, Part I, Quinazolinones", D. J. Brown, Ed., Interscience Publishers, New York (1967).

A trend toward sedative-hypnotic and anticonvulsant activity emerged for 4(3H)-quinazolinones possessing both a 2-alkyl and a 3-aryl substitutient. Of this class, 2-methyl-3-o-tolyl-4(3H)-quinazolinone, or methaqualone, is presently marketed in the United States. Although it is prescribed as a sedative-hypnotic, originally it was synthesized as a potential analgesic.

Methaqualone is both a cyclic amide and a pyrimidine derivative and as such has a formal structural resemblance to piperidone and barbiturate hypnotics; a comparison of the pharmacologic properties reveals that it is comparable to short-acting barbiturates in terms of sedative-hypnotic activity.

Methaqualone is superior to sodium phenobarbitone in preventing pentylenetetrazol (Metrazol) induced convulsive seizures in mice, while phenobartital is a better protector against maximal electro-shock seizures (MES) then methaqualone. Compounds which afford protection against Metrazol-induced seizures may be useful as anticonvulsants for the treatment of petit mal epilepsy, while protection against MES induced convulsions is indicative of possible activity as an anticonvulsant for the prevention of grand mal epileptic seizures; see Epilepsia 10:315 (1969).

The hypnotic and anticonvulsant properties of 4(3H)-quinazolinones have been demonstrated by many investigators, and several studies of structure-activity relationships have been conducted, e.g. see K.-H. Boltze, H.-D. Dell, H. Lehwald, D. Lorenz and M. Ruberg-Schwerer, Arzneim.-Forsch., 13, 688 (1963); C. Bianchi and A. David, J. Pharm. Pharmacol., 12, 501 (1960); C. M. Gupta, A. P. Bhaduri and N. M. Khanna, Indian J. Chem., 7, 866 (1969); G. E. Hardtmann, B. S. Huegi, J. H. Gogerty, L. C. Iorio and H. W. Barnes, J. Med. Chem., 14, 878 (1971); and V. M. Gushina, Nauch. Tr. Perm. Farm. Inst., 2, 2 (1967); Chem. Abstr., 70 27370c (1969). Boltze and associates have found that introduction of substituents onto the quinazolinone nucleus of methaqualone or reduction to the 1,2-dihydro derivative abolishes depressant activity. The lack of hypnotic activity in the 5,6,7,8-tetrahydro derivative of methaqualone indicates that planarity of the entire bicyclic system is essential for such activity. Other integral parts of the quinazolinone ring which appear to be necessary for sedative-hypnotic activity include the carbon at position 8, the 3-amide nitrogen, the carbonyl oxygen and the 2-methyl group. The methyl group of the 3-o-tolyl residue of methaqualone can be replaced by substituents such as bromo, chloro, fluoro, methoxy, hydroxy or amino without much loss of depressant activity.

It has also been reported that certain substituents on the 3-aryl residue decrease the hypnotic effect while enhancing anticonvulsant activity. This has been observed in the following changes in the 3-o-tolyl group:

(1) Introduction of an additional 4-amino, 3-chloro or 4-chloro substituent, or (2) Exchange of the o-methyl group for a 4-bromo or 4-chloro substituent.

Although it appears that the cause for separation of hypnotic and anticonvulsant activity may be a function of ortho vs. para substitution of the 3-aryl group, it has been observed that 2-methyl-3-o-chlorophenyl-4(3H)-quinazolinone (mecloqualone) is a better anticonvulsant agent than methaqualone and that 2-methyl-3-(p-diethylaminophenyl)-4(3H)-quinazolinone is of equal hypnotic activity to methaqualone.

Anticonvulsant activity can also be enhanced by adding certain substituents around the perimeter of the quinazolinone ring while keeping the 3-o-tolyl group unchanged. For example, addition of a 6-chloro group or a larger alkyl group at the 2 position increases the anticonvulsant activity at the expense of sedative-hypnotic action. Anticonvulsant activity also emerges when the 2-substituent is a 2-arylethenyl derivative. Such compounds have been prepared in low yields by reacting methaqualone with various aromatic aldehydes in the presence of alkali alkoxides. Boltze, et al, have shown that anticonvulsant activity is greatest when Ar=2-pyridyl.

In early 1974, there were only about a dozen marketed antiepileptic drugs in the United States; no new drug had received FDA approval as an antiepileptic since 1960. Although clinicians estimate that the commercial antiepileptic drugs controlled seizures in 70–80% of patients, a National Institute of Neurological and Communicative Disorders and Stroke (NINCDS) survey of the literature in 1970 failed to reveal data that substantiated such efficacy. In addition, there are certain types of seizures for which there are no specific drugs and others for which controlling therapy is accompanied by significant toxicity. There can be no doubt that new agents with greater specificity and less toxicity would mean significant therapeutic advances in the treatment of epilepsy.

OBJECTS OF THE INVENTION

Accordingly, it is a general object of the present invention to provide a new series of 2,3-disubstituted-4(3H)-quinazolinones.

Another object of this invention is to provide new compounds having antiepileptic activity comparable to or better than that of methaqualone.

A further object of this invention is to provide compounds having good anticonvulsant activity with little or no neurotoxicity.

An additional object of this invention is to provide such compounds which posses sedative-hypnotic and/or anticonvulsant activity.

Still another object of this invention is to provide methods and intermediates for the preparation, and methods and compositions for the use, of such compounds as sedative-hypnotic and/or anticonvulsant agents.

Upon study of the specification and appended claims, further objects and advantages of this invention will become apparent to those skilled in the art.

SUMMARY OF THE INVENTION

Briefly, the above and other objects, features and advantages of the present invention are attained in one aspect thereof by providing a 2-ketoalkyl-4(3H)-quinazolinone of the Formula V.

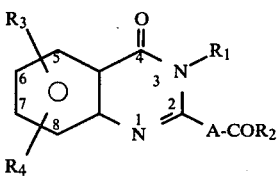

wherein $R_1$ is an aliphatic, cycloaliphatic or hydrocarbon aromatic group of 1–10 carbon atoms;

A is divalent alkylene of 1–10 carbon atoms;

$R_2$ is an aliphatic, cycloaliphatic, hydrocarbon aromatic or heterocyclic group of 1–10 carbon atoms formed by condensing an acyl ester of the formula $R_2COOR'$ which can be dissociated to form —$COR_2$ and R'OH in which R' is the alcoholic portion of said ester; and $R_3$ and $R_4$ are each hydrogen, hydroxy, amino, halogen, trifluoromethyl, alkyl, alkoxy, alkylthio or alkylsulfonyl each of 1–4 carbon atoms.

DETAILED DESCRIPTION

The starting materials used to prepare the compounds of the present invention are 2-alkyl-4(3H)-quinazolinones which are well known in the art or obtainable by synthetic methods well known to those skilled in the art to which this invention pertains. The only constraints in selecting suitable starting materials appears to be that any free hydroxyl or amino groups must be masked by means well known in the art and that no nitro groups be present in the reactants. Compounds in which $R_1$ is hydrogen are preferably first substituted at the 3-N position by conventional N-alkylation or N-arylation techniques to introduce the desired substituent $R_1$. Compounds in which the substituent at the 2-position is methyl and $R_1$ has any of the above-indicated values can be regiospecifically extended to any desired chain length at the 2-position following the methods reported by Murray et al in J.Org.Chem 39:595 (1974). $R_3$ and $R_4$ are both preferably hydrogen but can have any of the above-indicated values as is well known in the art. The 2-alkyl-4(3H)-quinazolinone starting material is an anion precursor which is converted to a dianion when $R_1$=hydrogen and the 2-alkyl group is methyl or a monoanion at the latter position when $R_1$ is other than hydrogen. The anion is formed by reaction of the precursor with a basic condensing agent in an inert, aprotic ionization solvent, e.g. lithium diisopropylamide (LDA) in tetrahydrofuran-hexane at 0° C. or an excess of sodium hydride in refluxing 1,2-dimethoxyethane (DME) as the reaction medium. The lateral carbanionic site then formed at the 2-position reacts rapidly and regiospecifically with electrophilic esters of the formula $R_2COOR'$ wherein $R_2$ and R' have the above-indicated values. As the ester condensation reaction introduces —$COR_2$ onto the 2-alkyl substituent of the 4(3H) quinazolinone nucleus with the formation of a by-product R'OH, the exact nature of R' is not critical and will normally be selected for reasons of availability, economy and ease of removal from the reaction mixture. R' will thus generally be alkyl of 1–4 carbon atoms. Suitable basic condensing agents include but are not limited to sodium hydride, potassium hydride, sodium amide, potassium amide, butyllithium, sodium methylate, sodium ethylate and potassium ethylate. Preferred are LDA which can be used analogously to the manner reported by Wasserman et al in Tetrahedron Letters 21:1731 (1975) and sodium hydride which can be used analogously to the manner reported by Wolfe et al in J.Org.Chem 39:2006 (1974), the contents of which are incorporated by reference herein.

Suitable inert solvents include but are not limited to benzene, toluene, xylene, monochlorobenzene, dimethyl acetamide, diethyl acetamide, dimethyl formamide, ether, tetrahydrofuran, dioxane, dimethylsulfoxide and mixtures thereof.

The reaction is generally effected at a temperature within the range of from room temperature to the boiling point of the solvent depending on the kind of ester and solvent used.

Since the compounds of Formula V form tautomers of keto and enol forms, the desired tautomer can be easily separated by using a conventional method such as fractional crystallization or chromatography.

A basic compound of Formula V can be converted into the associated acid addition salt with the use of an acid. For this reaction, suitable acids are those yielding physiologically acceptable salts. Suitable organic and inorganic acids are well known in the art and include but are not limited to aliphatic, alicyclic, araliphatic, aromatic and heterocyclic mono- or polybasic carboxylic or sulfonic acids, e.g. formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboyxlic acids, sulfamic acid, benzoic acid, salicyclic acid, nicotinic acid, isonicotinic acid, methanesulfonic acid, ethanedisulfonic acid, β-hydroxyethanesulfonic acid, p-toluenesulfonic acid, naphthalene-mono- and -disulfonic acids, sulfuric acid, nitric acid, hydrohalic acids, e.g., hydrochloric acid and hydrobromic acid, and phosphoric acids, e.g., orthophosphoric acid.

Divalent alkylene is generally of 1–8 carbon atoms, preferably of 1–3 carbon atoms. While linear alkylenes are most preferred, e.g., methylene, ethylene, trimethylene, tetramethylene, pentamethylene, hexamethylene, etc., lower alkyl substituted alkylenes of 1–3 carbon atoms, preferably of 1–2 carbon atoms, are also suitable, e.g., methylethylene, methylpropylene, ethylethylene ethylpropylene, etc. Preferably, the alkyl substituent is substituted on a non-terminal carbon atom, e.g., 2-methylpropylene, 2-ethylpropylene, etc.

Also suitable although not presently preferred is olefinically unsaturated divalent alkylene of 2–8 carbon atoms, preferably of 2–4 carbon atoms, e.g., vinylene, propenylene, etc. As with their saturated analogues, these groups can be linear or branched, e.g., 4-propyl-2-pentenylene.

Aliphatic or cycloaliphatic is preferably of up to 6 carbon atoms, e.g., alkyl, alkenyl, cycloalkyl or cycloalkenyl. Suitable alkyl groups include but are not limited to methyl, ethyl, n-propyl, isopropyl, n-butyl, isobutyl, sec.-butyl and tert.-butyl. Suitable alkenyl groups include but are not limited to vinyl, 2,2-dimethylvinyl, allyl, dimethylallyl, 1-propenyl, 1-butenyl, 2-butenyl, 3-methyl-2-butenyl, 1-pentyl and 2-pentyl. Suitable cycloalkyl groups include but are not limited to cyclopropyl, cyclobutyl, cyclopentyl and cyclohexyl, optionally substituted. e.g., by alkyl or alkenyl of up to 4 carbon atoms to form cycloalkylalkyl or cycloalkylalkenyl, e.g., cyclopropylmethyl. Suitable cycloalkenyl groups include but are not limited to cyclobutenyl, cyclopentenyl and cyclohexenyl optionally substituted, e.g., by alkyl or alkenyl of up to 4 carbon atoms to form cycloalkenylalkyl or cycloalkenylalkenyl, e.g., cyclobutenylethyl.

Hydrocarbon aromatic can be aryl, aralkyl, aralkenyl, or alkaryl or alkenylaryl of 6–10 ring carbon atoms and 1–6, preferably 1–3, alkyl or alkenyl carbon atoms and can be optionally substituted by 1–3 of hydroxy, halogen or amino. Aryl is preferably phenyl, naphthyl or phenyl mono- or di-substituted by at least one member selected from the group consisting of alkyl, alkoxy, alkylmercapto, monoalkylamino, dialkylamino or alkanoylamino wherein the alkyl, alkoxy and alkanoyl each are of up to 4 carbon atoms, F, Cl, Br, I, $CF_3$, OH, methylenedioxy and $NH_2$. Aralkyl is preferably phenylalkyl or substituted phenalkyl of 1–4 carbon atoms in the alkyl substituent, e.g. benzyl or phenethyl. Aralkenyl is preferably phenylalkenyl of 2–6 carbon atoms in the alkenylsubstituent, e.g. phenalkyl. Alkenylaryl is preferably alkenylphenyl of 2–6 carbon atoms in the alkenyl substituent, e.g. allylphenyl.

Monovalent heterocyclic ring substituents encompassed by the present invention are generally of 5–10, preferably 5 or 6 ring atoms of which 1–4, generally 1–3 and preferably 1 or 2, are oxygen, nitrogen and/or sulfur heteroatoms. the heterocyclic ring can be nonhydrogenated, e.g., imidazolinyl, oxazolinyl, thiazolinyl, thiazolinyl, etc.; or completely hydrogenated, e.g., piperazinyl, morpholino, tetrahydropyrimidinyl, etc.

Suitable heterocyclic groups can be those derived from a five member heterocyclic ring containing a single heteroatom, e.g., furyl, thienyl or pyrrolyl; a five member heterocyclic ring containing two heteroatoms, e.g., pyrazolyl, imidazolyl, oxazolyl, oxazolinyl, isoxazolyl, isoxazolinyl, thiazolyl or thiazolinyl; a five member heterocyclic ring containing 3 heteroatoms, e.g., thiazolyl, oxadiazolyl, thiadiazolyl, dioxanzolyl and oxathiazolyl; or a five member heterocyclic ring containing 4 heteroatoms, e.g., tetrazolyl, oxatriazolyl and thiatriazolyl. Preferred heterocyclic groups derived from a five member heterocyclic ring are furyl, thienyl, pyrrolyl, pyrazolyl, imidazlyl, isoxazolyl and thiazolyl, especially pyrrolyl and pyrazolyl.

Suitable heterocyclic groups can also be those derived from a six member heterocyclic ring containing a single heteroatom, e.g., pryidyl, pyranyl and thiopyranyl, preferably pyridyl; a six member heterocyclic ring containing two heteroatoms, e.g., dioxinyl, pyridazinyl, pyrimidinyl, pyrazinyl, piperazinyl, oxazinyl and morpholino; or a six member heterocyclic ring containing 3 ring heteroatoms, e.g., triazinyl, oxathiazinyl and oxadiazinyl. Preferred heterocyclic groups derived from a six member heterocyclic ring are pyridyl, pyridazinyl, pyrimidinyl, piperazinyl and morpholino, especially 3-pyridyl and 4-pyridyl.

Suitable acyl groups are the physiologically acceptable acyl groups of acids conventionally employed for the esterificiation of alcohols. Preferred are acyl groups of hydrocarbon carboxylic acids and hydrocarbon sulfonic acids, each of 1–5 carbon atoms. Especially preferred as acyl groups are alkanoyl and alkanesulfonyl of 1–7 carbon atoms, e.g., the acyl radicals of formic, acetic, propionic, butyric, isobutyric, valeric and enanthic acid, and of methanesulfonic, ethanesulfonic, propane- and isopropanesulfonic and butanesulfonic acid.

Contemplated as equivalents of the acyl radicals of alkanesulfonic acids are those of other aliphatic, cycloaliphatic and aromatic sulfonic acids of 1–15 carbon atoms. Such equivalent aliphatic sulfonic acids can be substituted, for example, by halogen, e.g., chlorine, or by an amino group and include but are not limited to the acyl radicals of cyclopentane- and cyclohexanesulfonic acids, benzensulfonic acid, p-toluenesulfonic acid and p-chlorobenzenesulfonic acid, as well as N,N-disubstituted aminosulfonic acids wherein the two substituents are each alkyl of 1–6 carbon atoms or alkylene of 4–6 members optionally interrupted by a nitrogen, oxygen or sulfur hereto atom, e.g., N,N-dimethylaminosulfonic acid, N,N-diethylaminosulfonic acid, N,N-bis($\beta$-chloroethyl) aminosulfonic acid N,N-diisobutylaminosulfonic acid, N,N-dibutylaminosulfonic acid, pyrrolidino-, piperidino-, piperazino-, N-methylpiperazino- and morpholinosulfonic acids.

Although alkanoyl and alkanesulfonyl of 1–7 carbon atoms are especially preferred, other acyl groups contemplated as equivalents are those of the above formula containing the acyl group of another organic hydrocarbon carboxylic acid, especially an aliphatic carboxylic acid, e.g., an alkanoic acid of 8–12 carbon atoms which can be unsaturated, branched, polybasic or substituted in the usual manner, e.g., by hydroxy or halogen atoms; a cycloaliphatic, aromatic or mixed aromatic-aliphatic (alkaryl and aralkyl) acid which can likewise be substituted in the usual manner; such equivalent acids include but are not limited to caproic acid, enanthic acid, undecyclic acid, oleic acid, dichloroacetic acid, cyclopentylpropionic acid, phenylpropionic acid, phenylacetic acid, phenoxyacetic acid, succinic acid and benzoic acid; others are acids containing 1–18, preferably 2–12 carbon atoms, including an aliphatic acid containing 1–18, preferably 1–6 carbon atoms, e.g., $\alpha$-ethylvaleric, 2-ethylbutyric, hexanoic, diethylacetic, triethylacetic, enanthic, octanoic, undecyclic and palmitic acid; a cyclic acid, preferably a cycloaliphatic acid, containing 5–18 carbon atoms, e.g., cyclopropylideneacetic, cyclobutylcarboxylic, cyclopentylcarboxylic, cyclopentylacetic, $\beta$-cyclopentylpropionic, cyclohexylacetic, cyclohexylacetic and $\beta$-cyclohexylpropionic acid; a carbocyclic aryl or alkaryl acid containing 6–18 carbon atoms and 1 to 5, preferably 1 or 2 rings, e.g., benzoic, 2-, 3-, or 4-methylbenzoic, 2,3-, 2,4-, 2,5-, 2,6-, 3,4- and 3,5-dimethylbenzoic, ethylbenzoic, 2,3,6-trimethylbenzoic and 3-methyl-$\alpha$-naphthoic acid; an aralkyl acid containing 7–18 carbon atoms, e.g., $\beta$-phenylpropionic acid; a polybasic acid containing 2–18 carbon atoms and 1 to 5 hydroxy groups, e.g., glycolic, lactic, citric, tartaric, d-maleic, d-glyceric and salicyclic acid; and the corresponding acids containing one, two or more simple substituents, e.g., halo, alkoxy, alkanoyloxy, etc. in the molecule, e.g., chloroacetic, fluoroacetic, trichloroacetic, trifluoroacetic, 2,3,4,-trimethoxybenzoic, phenoxyacetic and $\alpha$-naphthoxyacetic acid.

So that the activity and characteristic structure of the compounds of Formula V are predominantly that of a 2-ketoalkyl-4(3H) quinazolinone, the sum of the molecular weights of the substituents thereon is generally less than about 200, preferably less than about 150, and these substituents preferably contain a total of not more than 10 carbon atoms and not more than 5 heteroatoms. Preferred compounds of Formula V are those which show useful sedative-hypnotic activity, especially those which exhibit useful anticonvulsant activity at dosages lower than their sedative-hypnotic activity dosages.

Presently preferred compounds of the present invention are those compounds of Formula V, especially the subgeneric compounds of Formula III and Formula IV, in which the substituents defined therein have one or more of the following preferred values:

(a) Compounds wherein A is alkylene of 1-3 carbon atoms, especially methylene;

(b) Compounds wherein $R_1$ is alkyl of 1-3 carbon atoms, especially methyl and most especially as in (a);

(c) Compounds wherein $R_1$ is alkylphenyl of 1-3 carbon atoms in the alkyl group, especially o-tolyl or p-tolyl and most especially as in (a);

(d) Compounds wherein $R_1$ is halophenyl or dihalo phenyl, especially o- or p-chlorophenyl, o- or p-bromophenyl, dichlorophenyl or dibromophenyl and most especially as in (a);

(e) Compounds wherein $R_2$ is alkyl of 1-3 carbon atoms especially methyl and most especially as in (a), (b), (c) and (d);

(f) Compounds wherein $R_2$ is alkenyl of 2-5 carbon atoms, especially as in (a), (b), (c) and (d);

(g) Compounds wherein $R_2$ is pyridyl, most especially as in (a), (b), (c), and (d);

(h) Compounds wherein at least one of $R_3$ and $R_4$ is hydrogen, especially as in (a), (b), (c), (d), (e), (f) and (g); and (i) Compounds wherein $R_3$ and $R_4$ are both hydrogen, especially as in (a), (b), (c), (d), (e), (f) and (g).

2-Substituted-2-aryl-4-(3H)-quinazolinones of Formula V are normally prepared by two general methods. The first method involves cyclization of appropriate anthranilic acid derivatives with various other reactants. For instance, N-acylated anthranilic acids (Formula I, $R_1$=OH, $R_2$=CO-alkyl) may be reacted with aromatic amines in the presence of phosphorous trichloride to give 4(3H)-quinazolinones (Formula II where $R_3$=Ar and $R_4$=alkyl). This particular method is extensively employed for preparing compounds of Formula V wherein $R_4$=CH_3. Compounds of Formula V wherein $R_4$ is alkyl can also be prepared by condensing o-aminobenzanilide derivatives (Formula I, $R_1$=NHAr; $R_2$=H) with aliphatic acids.

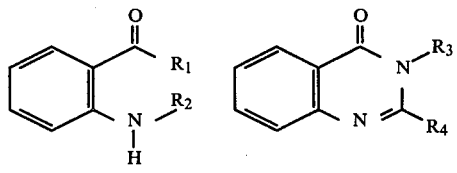

Formula I      Formula II

Direct cyclization of anthranilic acid derivatives of Formula I wherein $R_1$=NHAr and $R_2$=CO-alkyl can be used to prepare compounds of this type.

2,3-Diaryl-4(3H)-quinazolinones (Formula V, $R_3$=$R_4$=Ar) have been primarily prepared by direct cyclization of the corresponding anthranilic acid derivative (Formula I, $R_1$=NHAr, $R_2$=CO-aryl). These compounds can be prepared by the treatment of anthranilic acid with thioarylanilides in the presence of excess methyl anthranilate; a modified Willgerodt-Kindler reaction can also be used for the preparation of such compounds.

2-Halomethyl-3-aryl-4(3H)-quinazolinones, e.g. 2-chloromethyl derivatives ($R_4$=CH$_2$Cl) are prepared by direct cyclization of arylamides of N-chloroacetyl anthranilic acid. The 2-bromomethyl-3-aryl derivatives ($R_4$=CH$_2$Br) have been prepared by direct bromination of the corresponding 2-methyl-3-aryl derivatives with N-bromosuccinimide.

Treatment of anthranilic acid with aryl isothiocyanates yields the 2-thio-3-aryl derivatives ($R_4$=SH).

The second general method for preparing substituted 4(3H)-quinazolinones employs direct chemical modification of quinazolinones originally prepared by cyclization. For example, the 2-halomethyl derivatives may be employed as electrophilic reagents in reactions with various nucleophilic species to give the corresponding 2-substituted-3-aryl-derivatives wherein $R_4$=CH$_2$F, CH$_2$O$_2$CR, NH$_2$ NHR, NR$_2$, CH$_2$CN, CH$_2$O-Alkyl or -Aryl. Another large class of compounds, wherein $R_4$=S-alkyl, S-allyl, S-benzyl, S-phenacyl, S-acetonyl, etc. can be prepared by treating compounds where $R_4$=SH with suitable alkylating agents in alcoholic sodium hydroxide.

Direct functionalization of the 2-methyl group of 2-methyl-3-aryl-4(3H)-quinazolinones ($R_3$=aryl; $R_4$=methyl) has been achieved by base-catalyzed condensations with aromatic aldehydes to give styryl derivatives at the $R_4$ position. Similar compounds can be prepared by reation with aryl aldehydes in the presence of acetic acid-acetic anhydride. Such styryl compounds can be prepared in high yields by simply heating a mixture of the appropriate 2-methyl-4(3H)-quinazolinone and an aromatic aldehyde at 150°-180°. The success of this reaction is not deterred by the presence of a hydrogen, methyl, ethyl, phenyl, p-methoxyphenyl, and α or β-naphthyl groups on the amide nitrogen.

Condensations with aryl aldehydes are dependent on the lability of the protons of the lateral methyl of the appropriate 2-methyl-3-aryl-4(3H)-quinazolinone, which allows formation of a reactive intermediate. In the case of base catalysis, the intermediate is the resonance stabilized anion; in the acid catalyzed reactions, it is thought to be the prototopic tautomer. However, owing to the nature of the reaction conditions, these intermediates are present in only low equilibrium concentration. The success of these condensations is dependent upon dehydration of the appropriate aldol intermediates to drive the reaction to completion.

Acetylation of 2-methyl-1-phenyl-4(1H)-quinazolinone in refluxing acetic anhydride leads to the corresponding acetonyl derivative. The only previously known 2-acetonyl derivative of a 2,3-disubstituted-4(3H)-quinazolinone appears to be 2-acetonyl-3-methyl-4(3H)-quinazolinone, which was prepared by cyclization rather than side-chain acetylation.

Quaternary salts of 2-methyl-4(3H)-quinazolinones ($R_1$=H or alkyl; $R_2$=methyl) condense readily with aryl aldehydes to give both cis- and trans-2-styryl derivatives.

2-Methyl-4(3H)-quinazolinone undergoes condensation with phthalic anhydride at the fusion point of the mixture to give the respective phthalone, whereas anhydrous zinc chloride at 200° is necessary to bring about the same condensation with phthalimides.

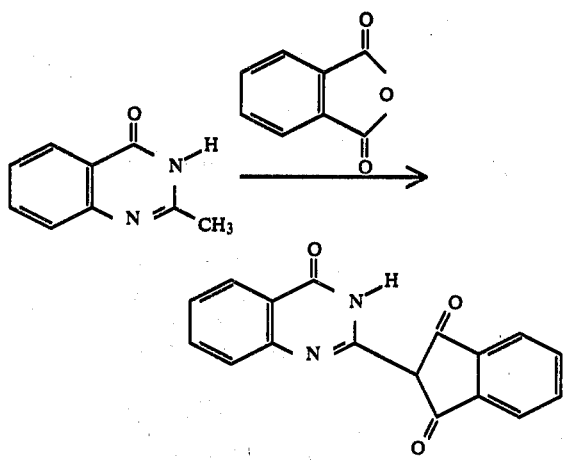

Due to their central nervous system (CNS) depressant activity, the compounds of this invention are useful as anticonvulsant agents in human and veterinary medicine. Because they exhibit useful anticonvulsant activity at dosages several fold lower than those which exhibit sedative-hypnotic activity, e.g., fourfold lower in the case of 2-[2-oxo-2-(4-pyridyl)ethyl]-3-o-chlorophenyl-4(3H)-quinazolinone, they are useful antiepileptic agents.

The compounds of this invention can be employed in mixture with conventional excipients, i.e., pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions or implants, including suppositories. Ampoules are convenient unit dosages.

For enteral application, particularly suitable are tablets, dragees, or capsules having talc and/or a carbohydraft carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–30 mg of a pharmaceutical carrier per each unit dosage and the amount of active agent of the invention per unit dosage is about 0.5 to 1.5 mg.

The compounds of this invention are generally administered to animals, including but not limited to mammals, e.g. laboratory animals, livestock, household pets, humans, cattle, cats, dogs, etc. An anticonvulsant effective daily dosage of the active compounds as administered intrapertoneally to mice generally comprises about 30 to 70 mg/kg, together with 1–5,000 mg. of pharmaceutically acceptable carrier. The dose can be administered singly or as divided dosages throughout the day.

Oral administration is preferred, the compounds of this invention being particularly valuable in the treatment of humans afflicted with epilepsy. In this regard, they can be employed in substantially the same manner as the known compounds Trimethadione and Ethosuximide for treatment of petit mal epilepsy and in substantially the same manner as the known compounds Dilantin and Phenobarbital for treatment of grand mal epilepsy.

It will be appreciated that the actual preferred amounts of active compounds used will vary according to the specific compound being utilized, the particular compositions formulated, the mode of application and the particular situs and organism being treated. Optimal application rates for a given set of conditions can be ascertained by those skilled in the art using conventional dosage determination tests in view of the above guidelines.

They are useful as intermediates in the production of other drugs, e.g., methaqualone by deacylation.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight. The values obtained in elemental analyses are within commonly accepted limits of error.

Thin Layer Chromatography (TLC) reported in the following Examples was performed on all compounds using Eastman chromagram sheets (silica gel) Type 6060 or EM sheets (silica gel), both of which contained fluorescent indicator. Developing solvents are indicated in the individual descriptions.

Vapor Pressure Chromatography (VPC) was performed using a Varian Aerograph model 90-P instrument with helium (60 ml/min.) as the carrier gas. The columns and temperatures employed are noted where appropriate.

EXAMPLE 1

Methaqualone was acylated with ethyl acetate, ethyl trifluoroacetate, ethyl picolinate, ethyl nicotinate, ethyl 1-adamantylcarboxylate, ethyl cinnamate and several esters of substituted benzoic acids to form corresponding 2-(2-ketoalkyl)quinazolinones of Formula III. The general procedure for preparing compounds III a–j involved addition of methaqualone and the appropriate ester (10% molar excess) to a slurry of excess sodium hydride in refluxing 1,2-dimethoxyethane (DME). The reaction was terminated after evolution of 2 equivalents of hydrogen (based on the amount of methaqualone) had occurred. Reaction periods ranged from one to five hours producing the acylated derivatives III a-j in yields of 19 to 85%.

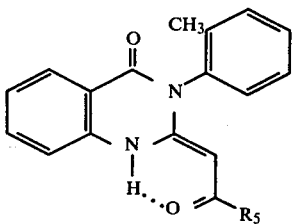

Formula III

| | |
|---|---|
| III a, $R_5$ = $CF_3$ | III h, $R_5$ = $C_6H_4Cl$-p |
| III b, $R_5$ = 2-pyridyl | III i, $R_5$ = $C_6H_4OCH_3$-p |
| III c, $R_5$ = 3-pyridyl | III j, $R_5$ = $C_6H_2(OCH_3)_3$-3,4,5 |
| III d, $R_5$ = 4-pyridyl | III k, $R_5$ = $C_6H_4NHCOCH_3$-p |
| III f, $R_5$ = CH=CH—$C_6H_5$ | III l, $R_5$ = $C_6H_4NHCOCF_3$-p |
| III g, $R_5$ = $C_6H_5$ | III m, $R_5$ = $CO_2C_2H_5$ |
| | III n, $R_5$ = $CH_3$ |

Departing from the general procedure, compounds III k and III l were prepared using ethyl p-acetamidobenzoate and ethyl p-trifluoroacetamidobenzoate, which were ionized with sodium hydride prior to the addition of methaqualone.

The yield of the 2-ethoxalylmethyl derivative III m was highest when methaqualone was added slowly to a mixture of excess sodium hydride and excess diethyl oxalate. In this way, the intermolecular condensation observed when the general acylation procedure was used was minimized.

EXAMPLE 2

Four other 2-methyl-3-aryl-4(3H)-quinazolinones of Formula II ($R_4$=methyl) and wherein $R_3$=o-chlorophenyl, phenyl, p-tolyl and p-bromophenyl, were similarly subjected to acylation by means of sodium hydride in order to obtain a series of compounds which might possibly exhibit CNS activity. Each of these four quinazolinones was acylated with ethyl trifluoroacetate, and the ethyl esters of picolinic, nicotinic and isonicotinic acid to give compounds of Formula IV a-p, respectively.

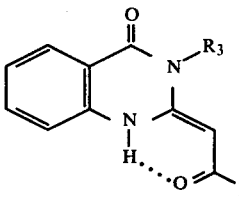

Formula IV

| | |
|---|---|
| IV a, $R_3$ = o-chlorophenyl; | $R_5$ = $CF_3$ |
| IV b, $R_3$ = o-chlorophenyl; | $R_5$ = 2-pyridyl |
| IV c, $R_3$ = o-chlorophenyl; | $R_5$ = 3-pyridyl |
| IV d, $R_3$ = o-chlorophenyl; | $R_5$ = 4-pyridyl |
| IV e, $R_3$ = phenyl; | $R_5$ = $CF_3$ |
| IV f, $R_3$ = phenyl; | $R_5$ = 2-pyridyl |
| IV g, $R_3$ = phenyl; | $R_5$ = 3-pyridyl |
| IV h, $R_3$ = phenyl; | $R_5$ = 4-pyridyl |
| IV i, $R_3$ = p-tolyl; | $R_5$ = $CF_3$ |
| IV j, $R_3$ = p-tolyl; | $R_5$ = 2-pyridyl |
| IV k, $R_3$ = p-tolyl; | $R_5$ = 3-pyridyl |
| IV l, $R_3$ = p-tolyl; | $R_5$ = 4-pyridyl |
| IV m, $R_3$ = p-bromophenyl; | $R_5$ = $CF_3$ |
| IV n, $R_3$ = p-bromophenyl; | $R_5$ = 2-pyridyl |
| IV o, $R_3$ = p-bromophenyl; | $R_5$ = 3-pyridyl |
| IV p, $R_3$ = p-bromophenyl; | $R_5$ = 4-pyridyl |
| IV q, $R_3$ = p-bromophenyl; | $R_5$ = $CH_3$ |
| IV r, $R_3$ = methyl; | $R_5$ = $C_6H_5$ |

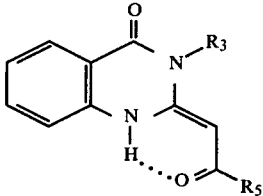

Formula IV

| | |
|---|---|
| IV s, $R_3$ = methyl; | $R_5$ = 3-pyridyl |

EXAMPLE 3

In addition, the 2-acetonyl derivative IV q was prepared from the corresponding bromophenyl starting material and IV r-s were formed by reacting 2,3-dimethyl-4(3H)-quinazolinone with methyl benzoate and ethyl nicotinate, respectively.

The $^1$H NMR spectra of all 2-(2-ketoalkyl)-3-aryl-4(3H)-quinazolinones examined revealed total enolization as evidenced by a broad enol proton singlet located between $\delta$ 15.8 and 14.8 and the presence of a vinyl singlet in the range of $\delta$ 5.9 to 4.4. This behavior was consistent with tautomerism previously observed in a variety of heterocyclic systems containing exocyclic $\beta$-carbonyl substituents. Assignment of the tautomeric enamine structures such as Formulae III and IV to these compounds is therefore arbitrary.

EXAMPLE 4

Preparation and Reactions of Metalated 2-Methyl-3-aryl-4(3H)-quinazolinones

A. Lateral Metalation of Methaqualone to Form Lithio Salt

The apparatus used in the metalation experiments consisted of a 100 ml three-necked flask equipped with magnetic stirring bar, rubber septum, ice bath and nitrogen inlet with a back pressure bubble valve. Solutions were added via a 25 ml pressure-equalizing addition funnel. To 0.7 g (5 mmol) of diisopropylamine in 40 ml of dry THF, was added 3.1 ml (5 mmol) of a 1.6 M solution of n-butyllithium in hexane. After 15 minutes, lithium diisopropylamide (LDA) was assumed to have formed and a solution of 1.25 g (5 mmol) of methaqualone in 10 ml of dry THF was added dropwise to the LDA solution. The dark red anion color appeared immediately and metalation to form the lithio salt was assumed to be complete after 20 minutes. The solution was then poured into 100 ml of cold water, which contained 10 ml of 1 N HCl. The organic phase was separated and the aqueous layer was extracted twice with 100 ml of ether. The organic layers were combined, dried (MgSO$_4$), filtered and concentrated. TLC analysis of the concentrate showed only one spot whose $R_f$ corresponded to that of methaqualone. The crude solid was recrystallized from isopropoanol to yield 1.15 g (86%) g of methaqualone mp 113°–115°. The $^1$H NMR spectrum was identical with that of an authentic sample.

B. 2-Ethyl-3-o-tolyl-4(3H)-quinazolinone

To a solution of 5 mmol of the thusly-prepared lithio salt in 75 ml of THF-hexane was added 0.71 g (5 mmol) of methyl iodide via syringe. The anion color disappeared within 2 minutes. After 30 minutes the reaction mixture was poured into 50 ml of cold water containing 10 ml of 1 N HCl. The resulting two phase mixture was extracted twice with 100 ml portions of ether. The ethereal layers were combined, dried (MgSO$_4$) and concentrated. The resulting light yellow solid was recrystallized from isopropanol-hexane to afford 0.69 g (53%) of the title compound, mp 93°–94° $^1$H NMR (CDCl$_3$) δ 8.33 (d, J=8 Hz, 5-H), 7.89–7.09 (m, 7H, aromatic), 2.39 (q, J=7 Hz, 2H, CH), 2.14 (s, 3H, CH$_3$) and 1.23 ppm (t, J=7 Hz, 3H, CH$_3$); ir (KBr) 1670 cm$^{-1}$ (C=O).

C. 2-[bis(Phenylthio)methyl]-3-o-tolyl-4(3H)-quinzaolinone

To a solution of 5 mmol of the lithio derivative prepared as described previously, in 60 ml of THF-hexanediisopropylamine, was added 1.24 g (5.7 mmol) of diphenyl disulfide in 15 ml of dry THF. The anion color disappeared gradually over a period of 45 minutes. After a total reaction time of 1.5 hr., the yellow orange solution was poured into 100 ml of saturated solution of sodium carbonate. The organic layer was separated and the aqueous layer was extracted twice with 100 ml portions of chloroform. The organic layers were combined and extracted once with 50 ml of water containing 7 ml of 1 N HCl. The organic layer was then dried (MgSO$_4$), filtered and concentrated. The resulting orange oil was chromatographed on silica gel. Elution with hexane-ether (98:2) afforded 0.38 g (31%) of recovered diphenyl disulfide, mp 60°, mmp with an authentic sample 59°–60°. The ir (KBr) spectrum was identical with that of an authentic sample.

Elution with hexane-ether (85:15) afforded 0.56 g (24%) of product, mp 139°–142°. Recrystallization from hexane-ether raised the mp to 142°–143°: $^1$H NMR (CDCl$_3$) δ 8.34 (d, J=8 Hz, 1H, 5H) and 7.93–6.87 (m, 17H, aromatic), 4.97 (s, 1H, CH) and 2.08 ppm (s, 3H, CH$_3$): mass spectrum (m/e) 467 (m+); ir (KBr) 1670 cm$^{-1}$ (C=O).

Anal. Calcd for C$_{28}$H$_{22}$N$_2$OS$_2$: C, 72.07; H, 4.75; N, 6.00. Found: C, 72.35; H, 5.08; N, 6.28.

Final elution of the column with hexane-ether (1:1) yielded 0.65 g (52%) of recovered methaqualone, mp 112.5°–114°. The $^1$H NMR spectrum was identical with that of an authentic sample of methaqualone. No monosulfenylated derivative of methaqualone could be isolated.

EXAMPLE 5

Phenylation of Potassio Salt to Give 2-Benzyl-3-o-tolyl-4(3H)-quinazolinone

The reaction was performed in a cylindrical pyrex vessel having an inside diameter of 4.2 cm and a height of 43 cm. This flask was equipped with a magnetic stirrer and a three-necked adapter to which a solid carbon dioxideisopropanol condenser fitted with a nitrogen inlet was attached. To a stirred suspension of (10 mmol) potassium amide, prepared from 0.40 g (10 mg-atom) of potassium in 300 ml of anhydrous liquid ammonia and a catalytic amount of ferric nitrate, was added 2.50 g (10 mmol) of methaqualone as a solid through a long-stemmed funnel. The deep red anion color of methaqualone appeared immediately and a dissolution period of 1 hour was then allowed. To the resulting solution was added 3.06 g (15 mmol) of iodobenzene in 30 ml of dry ether, and the reaction flask was lowered into the photoreactor and irradiated for 1 hour. The red solution was then quenched by carefully adding 1 g of solid ammonium chloride. The condenser was removed and the ammonia was evaporated while 150 ml of ether was added. Water (150 ml) was added to the resulting suspension. The organic phase was separated and the aqueous phase was extracted twice with 100 ml portions of chloroform. The organic phases were combined, dried (MgSO$_4$) and concentrated. By TLC analysis (chloroform) and comparison of the R$_f$ values, the broad leading spot and slowest moving spot were identified as iodobenzene and methaqualone, respectively. The yellow oil was chromatographed on silica gel. After the residual iodobenzene had been washed off the column with hexane, elution with hexane-ether (9:1) afforded ca. 15 mg of a clear nonviscous oil: $^1$H NMR (CDCl$_3$) 8.28 (d, J=8, 1H, 5-H), 7.73–6.83 (m, 17H, aromatic), 5.08 (s, 1H, CH) and 2.93 ppm (s, 3H, CH$_3$). Attempts to cause crystallization failed and no further characterization was carried out. Elution with hexane-ether (80:20) yielded 0.55 g (34%) of product as white platelets, mp 113°–114° (lit. mp 113°): $^1$H NMR (CDCl$_3$) δ 8.27 (d, J=8 Hz, 1H, 5-H), 7.80–6.77 (m, 12H, aromatic), 3.84 (s, 2H, CH$_2$) and 1.67 ppm (s, 3H, CH$_3$); ir (KBr) 1660 cm$^{-1}$ (C=O).

Continued elution with hexane-ether (80:20) afforded 0.51 g (41%) of methaqualone, mp 112°–113°, mmp 112°–113°.

EXAMPLE 6

2-(2-Hydroxy-2-phenylethyl)-3-o-tolyl-4(3H)-quinazolinone

To a solution of 5 mmol of lithio salt prepared as described previously, in 50 ml of THF-hexane-diisopropylamine, was added 0.53 g (5 mmol) of freshly distilled benzaldehyde via syringe. The intensity of the anion color rapidly lessened upon the addition of each drop of benzaldehyde. After 3 minutes, the resulting clear yellow solution was poured into 100 ml of cold water containing 10 ml of 1 N HCl. The aqueous-THF solution was extracted three times with 100 ml portions of ether. The ethereal extracts were combined, dried (MgSO$_4$) and concentrated at room temperature. TLC analysis (hexane-ether-acetone, 70:25:5) of the yellow oil revealed a three-component mixture. The major component, the title compound, was located between the two minor components corresponding to the styryl derivative (greatest R$_f$) and methaqualone (smallest R$_f$).

Trituration of the oil with hexane afforded 0.91 g (51%) of crude product which was a yellow solid, mp 119°–128°Further purification by recrystallization of the yellow amorphous solid from solvents such as isoproponal, ethyl acetate, ether, benzene, hexane and combinations of these solvents were unsuccessful. TLC analysis revealed that recrystallization caused decomposition.

Hexane-ether solvent systems provided the best chromatographic separation. Elution with (90:10) gave 0.030 g of the title compound as a white solid, mp 136°–141°:$^1$H NMR (CDCl$_3$) δ 8.43 (d, J=8 Hz, 1H, 5-H), 8.00–7.00 (m, 12H, aromatic), 5.82 and 5.68 (s, 1H, OH), 5.36 and 5.26 (m, 1H, CH), 2.96–2.32 (m, 2H, CH$_2$), and 2.74 and 2.06 ppm (s, 3H, CH$_3$). The spectrum shows a consequence of rotational diastereomers, as is also the case for the following spectrum in DMSO: $^1$H NMR (DMSO-d$_6$) δ 8.18–7.05 (m, 12H, aromatic), 5.50 and 5.54 (s, 1H, OH), 5.40–5.03 (m, 1H, CH), 2.77–2.59 (m, 2H, CH$_2$), and 2.09 and 1.85 ppm (s, 3H, CH$_3$); ir (KBr) 1670 cm$^{-1}$ (C=O).

An analytical sample was obtained from a fraction which gave a solid, mp 137°–138°.

Anal. Calcd for C$_{23}$H$_{20}$N$_2$O$_2$: C, 77.51; H, 5.61; N, 7.86. Found: C, 77.31; H, 5.54; N, 7.90.

Continued elution with hexane-ether (80:20) afforded 0.1 g (8%) of recovered methaqualone, mp 114°–115°, mmp 114°–114°. The $^1$H NMR spectrum was identical with an authentic sample of methaqualone.

EXAMPLE 7

Formation of 2-acetonyl-3-o-tolyl-4(3H)-quinazolinone (III n) by Condensation of Lithio Salt with Excess Ethyl Acetate To a magnetically stirred solution of 5 mmol of LDA, prepared by mixing 2.1 ml (5 mmol) of n-butyllithium (2.4 M) and 0.71 g (7 mmol) of diisopropylamine in 25 ml of dy THF at 0° under nitrogen, was added 1.25 g (5 mmol) of methaqualone. After 30 minutes, the entire solution of lithio salt was transferred via syringe (50 ml) to an addition funnel which was attached to a three-necked 100 ml flask. The bottom half of the additional funnel was loosely enclosed in aluminum foil which formed a cup that held several small pieces of dry ice. To a solution of 4.40 g (50 mmol) of ethyl acetate in 60 ml of dry THF at 0°, was added dropwise the 5 mmol solution of lithio salt over a 65 minute period. After addition was complete, the clear yellow solution was poured into 100 ml of water containing 10 ml of 1 N NCl. The resulting solution was extracted twice with 200 ml portions of ether, which were combined, dried and concentrated. TLC analysis (ether-acetone, 98:2) revealed two spots, with methaqualone as the major component. Column chromatography afforded, on elution with hexane-ether (9:1), 0.14 g (8%) of 2-acetonyl-3-o-tolyl-4(3H)-quinazolinone (III n) as white crystals, mp 164°–165.6°. The $^1$H NMR spectrum was identical with samples prepared by the general sodium hydride acylation procedure described subsequently.

The above reaction was repeated but in the presence of 0.48 g (10 mmol) of sodium hydride so that any hydrogen that might be evolved from the reaction of the title compound with sodium hydride could be monitored manometrically. Evolution of hydrogen was not observed during the addition of the 5 mmol solution of the lithio salt of methaqualone nor for 30 minutes after addition was complete. TLC of a concentrate of this solution appeared to be similar to that of the concentrate obtained in the previous reaction. No further attempt at isolation of the reaction components was carried out.

EXAMPLE 8

Sodium Hydride Promoted Acylations of 2-Methyl-3-aryl-4(3H)-quinazolinones

A. Attempted Acylation of Quinaldine with Ethyl Acetate in the Presence of Excess Sodium Hydride To a refluxing slurry of 2.5 g (52 mmol) of 50% sodium hydride in 150 ml of DME as added 1.14 g (13 mmol) of ethyl acetate and 1.43 g (10 mmol) of quinaldine in 20 ml of dry DME. After a reaction period of 2.5 hours, hydrogen evolution ceased (290 ml at STP, 12.9 mmol). The cooled reaction mixture was quenched with 50 ml of cold water containing 9 ml of 6 M HCl. The solution was diluted with 100 ml of water, made basic with 5% sodium bicarbonate solution, and then extracted three times with 100 ml portions of ether which were combined, dried (MgSO$_4$) and concentrated at room temperature. VPC analysis of the yellow concentrate on 1% SE-52 on Chromasorb W (High performance) at 120° revealed the presence of ethyl acetoacetate and unreacted quinaldine. The presence of a trace amount of 2-acetonylquinoline was verified by TLC analysis (hexane-ether, 1:1).

B. Preparation of Ethyl Acetoacetate using Ethyl Acetate and Excess Sodium Hydride To a refluxing slurry of 2.5 g (52 mmol) of 50% sodium hydride in 150 ml of DME was added 1.14 g (13 mmol) of ethyl acetate in 20 ml of DME. After a reaction period of 1.5 hours, hydrogen evolution ceased (285 ml at STP, 12.7 mmol) and the reaction mixture was worked up as described above to give a 0.47 g (62%) of crude ethyl acetoacetate, which was identified by VPC.

C. 2-Acetonyl-3-o-tolyl-4(3H)-quinazolinone (III n)

To a refluxing slurry of 2.5 g (52 mmol) of 50% sodium hydride in 140 ml of DME was added 2.5 g (10 mmol) of methaqualone and 1.14 g (13 mmol) of ethyl acetate in 20 ml of dry DME. After a reaction period of 3.5 hours, 475 ml (21.2 mmol) at STP of hydrogen had evolved. Since no further hydrogen evolution occured during an additional half-hour, the reaction was processed as described above except that chloroform was used in the extractions in place of ether. TLC analysis (ether hexane, 2:1) revealed the presence of methaqualone, ethyl acetoacetate and the title compound. Trituration of the concentrate with hexane-ether afforded a solid which was recrystallized from isopropanol to yield 1.78 g (61%) of yellow tinted crystals, mp 161°–163°. An analytical sample was prepared by a second recrystallization from isopropanol, which raised the mp to 163°–164°: $^1$H NMR (CDCl$_3$) δ 14.98 (broad s, 1H, enol), 8.11 (d, J=8 Hz, 1H, 5-H), 7.76–7.06 (m, 7H, aromatic), 4.39 (s, 1H, vinyl), 2.18 (s, 3H, CH$_3$) and 1.98 ppm (s, 3H, CH$_3$); ir (KBr) 1680 cm$^{-1}$ (C=O).

Anal. Calcd for C$_{18}$H$_{16}$N$_2$O$_2$: C, 73.95; H, 5.52; N, 9.58. Found: C, 74.13; H, 5.60; N, 9.48.

D. General Acylation Procedure

The apparatus used in these reactions consisted of a 250 ml three-necked flask equipped with a magnetic stirring bar, a 50 ml pressure-equalizing addition funnel and an efficient condenser. The reflux condenser was connected at its upper end to a U-shaped drying tube charged with Drierite and moisture indicator. The drying tube was in turn connected to a Precision Scientific wet-test meter, or a 1000 ml gas buret. Both measurement devices were filled with water.

The following general method was employed for the preparation of all acylated compounds except for examples 8 o,p and q.

Yields of acylated products are based on the starting 2-methyl-3-aryl-4(3H)-quinazolinone and represent amounts obtained after one recrystallization of the crude product resulting from Methods A or B described below. In many instances no further treatment was required to produce an analytical sample. Melting points are those of analytical samples.

A 2.50 g (52 mmol) sample of 50% sodium hydride-mineral oil dispersion was washed with 30 ml of hexane and filtered, and the oil-free sodium hydride was quickly added to the reaction flask along with 150 ml of dry DME. The resulting gray slurry was brought to reflux and a solution of 10 mmol of the appropriate 2-methyl-3-aryl-4(3H)-quinazolinone and 11 mmol of the appropriate ester was added dropwise over a period of 15 minutes. When addition was completed, the stirred reaction mixture was allowed to reflux until the theoretical amount of hydrogen was evolved. The volume of hydrogen expected in each experiment was calculated using the following equation:

$$V_m = \frac{T_m}{T_s} \times \frac{P_s}{P_m - P^o_{H_2O}} \times n \times 10^3 \times 22.4$$

where subscript s represents conditions at STP, subscript m represents the conditions of the meter and n equals the theoretical number of moles of hydrogen. When hydrogen evolution ceased (2–10 hr.), the heating mantle was removed and the flask was allowed to cool to room temperature. To the thick reaction mixture was added dropwise 3.12 g (52 mmol) of acetic acid (Caution!), followed by 50 ml of cold water. The resulting mixture was transferred to a 500 ml separatory funnel and an additional 100 ml of water was added. The pH of the resulting aqueous solution or suspension was then tested. If the aqueous layer was acidic, 5% sodium bicarbonate solution was added until the aqueous layer became basic to pH paper. Chloroform (100 ml) was added to the basic solution, and from this point on the reaction mixtures were processed according to either Method A or Method B described below.

Method A: If no solid was present at the chloroform-water interface, the organic phase was separated and the remaining aqueous phase was extracted twice with 100 ml portions of chloroform. The organic extracts were combined, dried, ($MgSO_4$), filtered, concentrated and the crude products were recrystallized from appropriate solvents.

Method B: If a solid was present at the interface, it was collected by suction filtration. Method A was then followed, except that the initially collected solid was combined with the material obtained by concentration of the chloroform extracts befor recrystallization.

E. 2-(3,3,3-Trifluoroacetonyl)-3-o-tolyl-4(3H)-quinazoline(IIIa)

Preparation required 2.50 g (10 mmol) of methaqualone and 1.56 g (11 mmol) of ethyl trifluoroacetate with a reaction period of 2 hours, followed by workup Method A to afford a crude solid which on recrystallization from isopropanol-chloroform yielded 3.02 g (87%) of the title compound as white crystals, mp 194°–195°; $^1$H NMR ($CDCl_3$) δ 14.87 (broad s, 1H, enol), 8.41 (d, J=8 Hz, 1H, 5-H), 8.07–7.26 (m, 7H, aromatic), 4.92 (s, 1H, vinyl) and 2.23 ppm (s, 3H, $CH_3$); $^{19}$F NMR ($CDCl_3$) δ-94.3 ppm (s); ir (KBr) 1690 cm$^{-1}$ (C=O).

Anal. Calcd for $C_{18}H_{13}F_3N_2O_2$: C, 62.43; H, 3.78; N, 8.09. Found: C, 62.50; H, 3.81; N, 7.98.

F. 2-[2-Oxo-2-(2-pyridyl)ethyl]-3-o-tolyl-4-(3H)-quinazolinone (IIIb)

Treatment of 2.50 g (10 mmol) of methaqualone with 1.66 g (11 mmol) of ethyl picolinate for a period of 2 hours, followed by workup Method A, afforded a yellow-brown crude solid which was recrystallized from isopropanol-chloroform to give 2.84 g (80%) of product. An analytical sample ws prepared by one recrystallization from chloroform-hexane. The resulting light yellow crystals had mp 254°–255°; $^1$H NMR ($CDCl_3$) δ 15.48 (broad s, 1H, enol), 8.52–7.20 (m, 12H, aromatic), 6.01 (s, 1H, vinyl) and 2.25 ppm (s, 3H, $CH_3$); ir (KBr) 1690 cm$^{-1}$ (C=O).

Anal. Calcd for $C_{22}H_{17}N_3O_2$: C, 74.35; H, 4.82; N, 11.82. Found: C, 74.24; H, 4.98; N, 11.91.

G. 2-[2-Oxo-2-(3-pyridyl)ethyl]-3-o-tolyl-4(3H)-quinazolinone (IIIc)

Reaction of 2.50 g (10 mmol) of methaqualone and 1.66 g (11 mmol) of ethyl nicotinate for a period of 3 hours, followed by workup Method A, afforded a yellow crude product which was recrystallized from isopropanol to give 2.48 g (70%) of product. An analytical sample was prepared by one recrystallization from chloroform-hexane. The resulting yellow microcrystals had mp 234°–235°; $^1$H NMR ($CDCl_3$) δ 15.29 (broad s, 1H, enol), 8.78–7.25 (m, 12H, aromatic), 5.15 (s, 1H, vinyl) and 2.23 ppm (s, 3H, $CH_3$); ir (KBr) 1690 cm$^{-1}$ (C=O).

Anal. Calcd for $C_{22}H_{17}N_3O_2$: C, 74.35; H, 4.82; N, 11.82. Found: C, 73.98; H, 4.72; N, 11.66.

H. 2-[2-Oxo-2-(4-pyridyl)ethyl]-3-o-tolyl-4(3H)-quinazolinone(IIId)

Preparation required 2.50 g (10 mmol) of methaqualone and 1.66 g (11 mmol) of ethyl isonicotinate. After a reaction period of 2 hours and using workup Method B, the crude product was recrystallized from isopropanol-chloroform to give 3.02 g (85%) as yellow crystals, mp 219°–220°: $^1$H NMR ($CDCl_3$) δ 15.40 (broad s, 1H, enol), 8.62–7.12 (m, 12H, aromatic), 5.08 (s, 1H, vinyl) and 2.20 ppm (s, 3H, $CH_3$); ir (KBr) 1680 cm$^{-1}$ (C=O).

Anal. Calcd for $C_{22}H_{17}N_3O_2$: C, 74.35; H, 4.82; N, 11.82 Found: C, 74.42; H, 5.12; N, 11.62.

I. 2-[2-Oxo-P2-(1-adamantyl)ethyl]-3-o-tolyl-4(3H)-quinazolinone(IIIe)

Treatment of 2.50 g (10 mmol) of methaqualone with 2.3 g (11 mmol) of ethyl 1-adamantylcarboxylate (prepared from the acid chloride and excess absolute ethanol) for a reaction period of 3.5 hours and using workup Method A afforded a brown oil which solidified on standing. The crude product was recrystallized from isopropanol-chloroform-hexane to yield 3.3 g (81%). An analytical sample was prepared by one recrystallization from isopropanol-hexane. The resulting white crystals had mp 221°–222°: $^1$H NMR ($CDCl_3$) δ 15.82 (broad w, 1H, enol), 8.20 (d, J=8 Hz, 1H, 5-H), 7.72–7.16 (m, 7H, aromatic), 4.56 (s, 1H, vinyl), 2.18 (s, 3H, $CH_3$) and 2.06–1.48 ppm (m, 15H, CH and $CH_2$); ir (KBr) 1680 cm$^{-1}$ (C=O).

Anal. Calcd for $C_{27}H_{28}N_2O_2$: C, 78.61; H, 6.84; N, 6.79. Found: C, 78.23; H, 6.69; N, 6.64.

J. 2-(2-Oxo-4-phenylbut-3-enyl)-3-o-tolyl-4(3H)-quinazolinone (IIIf)

Reaction of 2.50 g (10 mmol) of methaqualone and 1.94 g (11 mmol) of ethyl cinnamate for a period of 2.5 hours, followed by workup Method A, afforded a brown oil which on trituration with hexane-ether gave a yellow solid that was recrystallized from isopropanol-ether to yield 0.64 g (19%) of product. An analytical sample was prepared by two recrystallizations from the same solvents. The resulting yellow crystals had mp 190°–191°: $^1$H NMR ($CDCl_3$) δ 16.18 (broad s, 1H, enol), 8.35 (d, J=8 Hz, 1H, 5-H), 7.97–7.23 (m, 13H, vinyl and aromatic), 6.55 (d, J=17 Hz, 1H, vinyl), 4.73 (s, 1H, vinyl) and 2.25 ppm (s, 3H, $CH_3$); ir (KBr) 1680 cm$^{-1}$ (C=O).

Anal. Calcd for $C_{25}H_{20}N_2O_2$: C, 78.98; H, 5.30; N, 7.37 Found: C, 78.99; H, 5.22; N, 7.10.

K. 2-(2-Oxo-2-phenylethyl)-3-o-tolyl-4(3H)-quinazolinone(IIIg)

Treatment of 2.50 g (10 mmol) of methaqualone with 1.5 g (11 mmol) of methyl benzoate for a period of 5 hours, followed by workup Method A, afforded a crude product that was recrystallized from isopropanol to yield 2.84 g (80%) of light yellow flakes, mp 216°–217°: $^1$H NMR (DMSO-$d_6$) δ 15.50 (broad s, 1H, enol), 8.18 (d, J[Hz, 1H, 5-H), 7.98–7.32 (m, 12H, aromatic), 5.07 (s, 1H, vinyl) and 2.19 ppm (s, 3H, CH$_3$); ir (KBr) 1680 cm$^{-1}$ (C=O).

Anal. Calcd for C$_{23}$H$_{18}$N$_2$O$_2$: C, 77.13; H, 5.12; N, 8.17. Found: C, 77.41; H, 5.04; N, 8.27.

L. 2-[2-Oxo-2-(4-chlorophenyl)ethyl]-3-o-tolyl-4(3H)-quinazolinone (IIIh)

Reaction of 2.50 g (10 mmol) of methaqualone and 1.88 g (11 mmol) of methyl p-chlorobenzoate for a period of 4 hours, followed by workup Method A, afforded a crude product that was recrystallized from chloroform-isopropanol to give 2.88 g (74%) of product, mp 227°–227.5°: $^1$H NMR (CDCl$_3$) δ 15.83 (broad s, 1H, enol), 8.36 (d, J=8 Hz, 1H, 5-H), 7.98–7.29 (m, 11H, aromatic), 5.15 (s, 1H, vinyl) and 2.25 ppm (s, 3H, CH$_3$); ir (KBr) 1680 cm$^{-1}$ (C=O).

Anal. Calcd for C$_{23}$H$_{17}$ClN$_2$O$_2$: C, 71.04; H, 4.41; N, 7.20. Found: C, 70.90; H, 4.37; N, 7.17.

M. 2-[2-Oxo-2-(4-methoxyphenyl)ethyl]-3-o-tolyl-4(3H)-quinazolinone (IIIi)

Reaction of 2.50 g (10 mmol) of methaqualone with 1.83 g (11 mmol) of methyl anisate for a period of 3 hours, followed by workup Method A, afforded a crude solid that was recrystallized from isopropanol to give 2.76 g (72%) of yellow crystals, mp 169°–170°: $^1$H NMR (CDCl$_3$) δ 15.79 (broad s, 1H, enol), 8.38 (d, J=8 Hz, 1H, 5-H), 7.98–6.94 (m, 11H, aromatic), 5.20 (s, 1H, vinyl), 3.92 (s, 3H, OCH$_3$) and 2.28 ppm (s, 3H, CH$_3$); ir (KBr) 1675 cm$^{-1}$ (C=O).

Anal. Calcd for C$_{24}$H$_{20}$N$_2$O$_3$: C, 74.98; H, 5.24; N, 7.29. Found: C, 75.16; H, 5.24; N, 7.59.

N. 2-[2-Oxo-2-(3,4,5-trimethoxyphenyl)ethyl]-3-o-tolyl-4(3H)-quinazolinone (IIIj)

Preparation required 2.50 g (10 mmol) of methaqualone and 2.49 g (11 mmol) of methyl 3,4,5-trimethoxybenzoate. After a reaction period of 4 hours and using workup Method A, the crude product was recrystallized from chloroform-hexane to yield 2.98 g (67%) of product. An analytical sample was prepared by a second recrystallization from the same solvents, mp 200°–201°: $^1$H NMR (CDCl$_3$) δ 15.54 (broad s, 1H, enol), 8.31 (d, J=8 Hz, 1H, 5-H), 7.93–7.30 (m, 7H, aromatic), 6.96 (s, 2H, phenyl), 5.08 (s, 1H, vinyl), 3.91 and 3.86 (two s, 9H, OCH$_3$), and 2.22 ppm (s, 3H, CH$_3$); ir (KBr) 1675 cm$^{-1}$ (C=O).

Anal. Calcd for C$_{26}$H$_{24}$N$_2$O$_2$: C, 70.26; H, 5.44; N, 6.30. Found: C, 70.39; H, 5.61; N, 6.06.

O. 2-[2-Oxo-2-(p-trifluoroacetamidophenyl)ethyl]-3-o-tolyl-4(3H)-quinazolinone (IIII)

To a stirred gray slurry of 1.26 g (30 mmol) of sodium hydride, as a 57% mineral oil dispersion in 100 ml of dry THF, was added a solution of 1.30 g (5 mmol) of ethyl p-trifluoroacetamidobenzoate in 30 ml of dry THF. After the evolution of hydrogen ceased, the resulting solution was brought to reflux and a solution of 1.25 g (5 mmol) of methaqualone in 30 ml of dry THF was added over a period of 15–20 minutes. After a reaction period of 5 hours, during which evolution of the theoretical volume of hydrogen occurred, the thick brown reaction mixture was cooled to room temperature and 1.8 g of acetic acid in 50 ml of cold water was added dropwise with caution to the reaction solution. The resulting solution was poured into 200 ml of water and the aqueous layer was made basic with 5% sodium bicarbonate solution. The organic layer was separated and the aqueous phase was extracted twice with 200 ml portions of chloroform. The organic phases were combined, dried (MgSO$_4$) and concentrated to give a brown solid. The brown solid was recrystallized from chloroform to give 1.09 g (47%) of product. An analytical sample was prepared by two additional recrystallizations from chloroform. The resulting yellow microcrystals melted at 278°–280°: $^1$H NMR (CDCl$_3$-50% by vol CF$_3$COOH) δ 8.85 (s, 1H, NH), 8.37–7.11 (m, 12H, aromatic) and 2.18 ppm (s, 3H, CH$_3$); ir (KBr) 3290 (NH) and 1690 cm$^{-1}$ (C=O).

The signals due to vinyl and methylene hydrogens are not reported since these protons appeared to be severely affected by the presence of the trifluoroacetic acid and only a broad peak centered at 4.76 ppm gave possible evidence for their presence.

Anal. Calcd for C$_{25}$H$_{18}$F$_3$N$_3$O$_3$: C, 64.51; H, 3.90; N, 9.03. Found: C, 64.35; H, 3.71; N, 9.24.

P. 2-[2-Oxo-2-(p-acetamidophenyl)ethyl]3-o-tolyl-4(3H)-quinazolinone (IIIk)

To a stirred gray slurry of 1.26 g (30 mmol) of sodium hydride, as a 57% mineral oil dispersion in 100 ml of dry THF, was added a solution of 1.04 g (5 mmol) of ethyl p-acetamidobenzoate in 30 ml of dry THF. After the evolution of hydrogen ceased, the resulting solution was brought to reflux and a solution of 1.25 g (5 mmol) of methaqualone in 30 ml of dry THF was added over a period of 15–20 minutes. After evolution of the theoretical amount of hydrogen (4 hours), the reaction mixture was cooled to room temperature and a solution of 1.8 g of acetic acid in 50 ml of cold water was added dropwise with caution to the reaction solution. The brown reaction mixture was poured into 200 ml of water and the resulting solution was extracted twice with 200 ml portions of chloroform. The chloroform extracts were combined, dried (MgSO$_4$) and concentrated to afford a yellow solid, which was recrystallized from chloroform to give 0.86 g (42%) of crude product. An analytical sample was prepared by three recrystallizations to give yellow microcrystals, mp 262°–275° (dec): $^1$H NMR (CDCl$_3$ 50% by vol CF$_3$CO$_2$H) δ 8.86 (m, 13H, NH and aromatics), 2.30 (s, 3H, CH$_3$) and 2.15 ppm (s, 3H, CH$_3$). The $^1$H NMR signals corresponding to the methylene and vinyl protons of the proposed formula showed the same behavior as those of product; ir (KBr) 3310 (NH) and 1680 cm$^{-1}$ (C=O).

Anal. Calcd for C$_{25}$H$_{21}$N$_3$O$_3$: C, 72.98; H, 5.14; N, 10.21. Found: C, 73.17; H, 5.32; N, 9.91.

Q. 2-Ethoxallylmethyl-3-o-tolyl-4(3H)-quinazolinone (IIIm)

This compound was prepared by inverse addition and not by the general acylation procedure. To a refluxing slurry of 1.05 g (25 mmol) of sodium hydride (57%) and 3.2 g (22 mmol) of diethyl oxalate in 140 ml of dry DME was added dropwise 1.25 g (5 mmol) of methaqualone in 40 ml of DME over a period of 4.5 hours. When addition was complete, the reaction was allowed to continue at reflux for an additional 45 minutes. The resulting yellow reaction mixture was processed as described in the general acylation procedures, followed by workup Method A. The resulting concentrate upon trituration with hexane-ether afforded a yellow solid that was recrystallized from isopropanol to give 1.08 g (62%) of product, mp 187°–190°.

A second recrystallization was required to produce the analytical sample, as yellow crystals, mp 191°–191.5°: $^1$H NMR (CDCl$_3$) δ 15.51 (broad s, 1H, enol), 8.35 (d, J=8 Hz, 1H, 5-H), 8.00–7.24 (m, 7H, aromatic), 5.47 (s, 1H, vinyl), 4.30 (q, J=7 Hz, 2H, CH$_2$), 2.21 (s, 3H, CH$_3$) and 1.35 ppm (t, J=7 Hz, 3H, CH$_3$); ir (KBr) 1710 and 1680 cm$^{-1}$ (C=O).

Anal. Calcd for $C_{20}H_{18}N_2O_4$: C, 68.56; H, 5.18; N, 8.00. Found: C, 68.42; H, 5.03; N, 7.88.

EXAMPLE 9

A. 2-(3,3,3-Trifluoroacetonyl)-3-o-chlorophenyl-4(3H)-quinazolinone (IVa)

This preparation was carried out with 2.7 g (10 mmol) of mecloqualone and 1.56 g (11 mmol) of ethyl trifluoroacetate for a reaction period of 1.5 hr. After using workup Method B, the resulting solid was recrystallized from isopropanol-chloroform to give 3.19 g (87%) of product as light yellow crystals, mp 158°–159°: $^1$H NMR (CDCl$_3$) δ 14.33 (broad s, 1H, enol), 8.19–7.20 (m, 8H, aromatic) and 4.74 ppm (s, 1H, vinyl); ir (KBr) 1685 cm$^{-1}$ (C=O).

Anal. Calcd for $C_{17}H_{10}ClF_3N_2O_2$: C, 55.68; H, 2.75; N, 7.63. Found: C, 55.78; H, 2.82; N, 7.80.

B. 2-[2-Oxo-2-(2-pyridyl)ethyl]-3-o-chlorophenyl-4(3H)-quinazolinone (IVb)

Preparation required 2.70 g (10 mmol) of mecloqualone and 1.66 g (11 mmol) of ethyl picolinate. After a reaction time of 2 hours, followed by workup Method B, a yellow solid was obtained which was recrystallized from chloroform-isopropanol to yield 3.08 g (82%) of yellow crystals, mp 240°–241°: $^1$H NMR (CDCl$_3$-DMSO-d$_6$) δ 15.44 (broad s, 1H, enol), 8.40–7.20 (m, 12H, aromatic) and 5.85 ppm (s, 1H, vinyl); ir (KBr) 1690 cm$^{-1}$ (C=O).

Anal. Calcd for $C_{21}H_{14}ClN_3O_2$: C, 67.12; H, 3.76; N, 11.18. Found: C, 67.25; H, 3.88; N, 11.24.

C. 2-[2-Oxo-2-(3-pyridyl)ethyl]-3-o-chlorophenyl-4(3H)-quinazolinone (IVc)

The reaction of 2.70 g (10 mmol) of mecloqualone and 1.66 g (11 mmol) of ethyl nicotinate was carred out for a period of 1.5 hours. After using workup Method A, the crude product which solidified on standing was recrystallized from chloroform-hexane to give 2.97 g (79%) of product. An analytical sample was prepared by an additional recrystallization from the same solvents. The resulting crystals had mp 235°–237°: $^1$H NMR (CDCl$_3$) δ 15.19 (broad s, 1H, enol), 8.72–7.18 (m, 12H, aromatic) and 5.05 ppm (s, 1H, vinyl); ir (KBr) 1680 cm$^{-1}$ (C=O).

Anal. Calcd for $C_{21}H_{14}ClN_3O_2$: C, 67.12; H, 3.76; N, 11.18. Found: C, 66.83; H, 3.44; N, 11.19.

D. 2-[2-Oxo-2-(4-pyridyl)ethyl]-3-o-chlorophenyl-4(3H)-quinazolinone (IVd)

Treatment of 2.70 g (10 mmol) of mecloqualone and 1.66 g (11 mmol) of ethyl isonicotinate for a reaction period of 2 hours, followed by workup Method B, yielded a crude product which was recrystallized from chloroform-isopropanol to give 3.46 g (92%) of product. An analytical sample was prepared by a recrystallization from chloroform. The resulting yellow crystals had mp 214°–215°: $^1$H NMR (CDCl$_3$) δ 15.36 (broad s, 1H, enol), 8.65–7.16 (m, 12H, aromatic) and 4.98 ppm (s, 1H, vinyl); ir (KBr) 1685 cm$^{-1}$ (C=O).

Anal. Calcd for $C_{21}H_{14}ClN_3O_2$: C, 67.12; H, 3.76; N, 11.18. Found: C, 67.43; H, 4.01; N, 11.28.

E. 2-(3,3,3-Trifluoroacetonyl)-3-phenyl-4(3H)-quinazolinone (IVe)

Reaction of 1.18 g (5 mmol) of 2-methyl-3-phenyl-4(3H)-quinazolinone and 0.78 g (5.5 mmol) of ethyl trifluoroacetate with 1.05 g (25 mmol) of sodium hydride (57%) for a period of 2 hours, followed by workup Method A, afforded a crude product which was recrystallized from chloroform-hexane to give 1.34 g (81%) of a white solid, mp 199°–200°: $^1$H NMR (CDCl$_3$) δ 14.88 (broad s, 1H, enol), 8.36 (d, J=8 Hz, 1H, 5-H), 8.05–7.34 (m, 8H, aromatic), and 4.94 ppm (s, 1H, vinyl); $^{19}$F NMR (CDCl$_3$) δ-94.3 ppm (s); ir (KBr) 1690 cm$^{-1}$ (C=O).

Anal. Calcd for $C_{17}H_{11}F_3N_2O_2$: C, 61.45; H, 3.34; N, 8.43. Found: C, 61.31; H, 3.30; N, 8.62.

F. 2-[2-Oxo-2-(2-pyridyl)ethyl]-3-phenyl-4(3H)-quinazolinone(IVf)

Treatment of 2.36 g (10 mmol) of 2-methyl-3-phenyl-4(3H)-quinazolinone and 1.66 g (11 mmol) of ethyl picolinate in 160 ml of THF for a reaction period of 2.5 hours, followed by workup Method A, afforded a yellow crude product which was recrystallized from chloroform-hexane to give 2.6 g (76%) of yellow crystals, mp 272°–273° (dec): $^1$H NMR (CDCl$_3$) δ 15.31 (broad s, 1H, enol), 8.27–7.02 (m, 13H, aromatic) and 5.90 ppm (s, 1H, vinyl); ir (KBr) 1680 cm$^{-1}$ (C=O).

Anal. Calcd for $C_{21}H_{15}N_3O_2$: C, 73.89; H, 4.43; N, 12.31. Found: C, 73.87; H, 4.13; N, 12.69.

G. 2-[2-Oxo-2-(3-pyridyl)ethyl]-3-phenyl-4(3H)-quinazolinone(IVg)

Preparation required 2.36 g (10 mmol) of 2-methyl-3-phenyl-4(3H)-quinazolinone and 1.66 g (11 mmol) of ethyl nicotinate. After a reaction period of 3.5 hours, and using workup Method A, the crude product was recrystallized from isopropanol-chloroform to yield 2.45 g (72%) of yellow crystals, mp 248°–249°: $^1$H NMR (CDCl$_3$) δ 15.38 (broad s, 1H, enol), 8.79–7.15 (m, 13H, aromatic) and 5.10 ppm (s, 1H, vinyl); ir (KBr) 1685 cm$^{-1}$ (C=O).

Anal. Calcd for $C_{21}H_{15}N_3O_2$: C, 73.89; H, 4.43; N, 12.31. Found: C, 74.02; H, 4.79; N, 12.46.

H. 2-[2-Oxo-2-(4-pyridyl)ethyl]-3-phenyl-4(3H)-quinazolinone(IVh)

Treatment of 2.36 g (10 mmol) of 2-methyl-3-phenyl-4(3H)-quinazolinone and 1.66 g (11 mmol) of ethyl isonicotinate in 160 ml of THF for a reaction period of 3.5 hours, followed by workup Method B, afforded a crude product which was recrystallized from chloroform-hexane to give 2.1 g (62%) of product. An analytical sample was prepared by a recrystallization from the same solvent system. The resulting yellow crystals had mp 241°–242°: $^1$H NMR (CDCl$_3$) δ 15.12 (broad s, 1H, enol), 8.48–7.02 (m, 13H, aromatic) and 5.02 ppm (s, 1H, vinyl); ir (KBr) 1685 cm$^{-1}$ (C=O).

Anal. Calcd for $C_{21}H_{15}N_3O_2$: C, 73.89; H, 4.43; N, 12.31 Found: C, 73.71; H, 4.40; N, 12.16.

I. 2-(3,3,3-Trifluoroacetonyl)-3-p-tolyl-4(3H)-quinazolinone(IVi)

Treatment of 1.25 g (5 mmol) of 2-methyl-3-p-tolyl-4(3H)-quinazolinone and 0.78 g (5.5 mmol) of ethyl trifluoroacetate with 1.05 g (25 mmol) of sodium hydride (57%) for a reaction period of 1.5 hours, followed by workup Method A, afforded a crude product which was recrystallized from isopropanol-chloroform to give 1.25 g (72%) of white crystals, mp 215°–216°: $^1$H NMR (CDCl$_3$) δ 14.89 (broad s, 1H, enol), 8.36 (d, J=8 Hz,1H, 5-H), 8.04–7.20 (m, 7H, aromatic), 5.02 (s,1H, vinyl) and 2.54 ppm (s, 3H, CH$_3$); $^{19}$F NMR (CDCl$_3$) δ-94.3 ppm (s); ir (KBr) 1690 cm$^{-1}$ (C=O).

Anal. Calcd for $C_{18}H_{13}F_3N_2O_2$: C, 62.43; H, 3.78; N, 8.09. Found: C, 62.17; H, 3.73; N, 8.16.

J. 2-[2-(Oxo-2-(2-pyridyl)ethyl]-3-p-tolyl-4(3H)-quinazolinone(IVj)

Preparation required 2.50 g (10 mmol) of 2-methyl-3-p-tolyl-4-(3H)-quinazolinone and 1.66 g (11 mmol) of ethyl picolinate. After a reaction period of 2.5 hours, followed by workup Method A, the crude produced was recrystallized from chloroform-hexane to yield 2.7 g (76%) of product. An analytical sample was prepared by one recrystallization from chloroform-hexane. The resulting yellow microcrystals had mp 268°–269°: $^1$H NMR (CDCl$_3$) δ 15.30 (broad s, 1H, enol), 8.29–7.20 (m, 12H, aromatic), 5.96 (s, 1H, vinyl) and 2.48 ppm (s, 3H, CH$_3$); ir (KBr) 1680 cm$^{-1}$ (C=O).

Anal. Calcd for C$_{22}$H$_{17}$N$_3$O$_2$: C, 74.35; H, 4.82; N, 11.82. Found: C, 74.01; H, 4.83; N, 11.91.

K.    2-[2-Oxo-2-(3-pyridyl)ethyl]-3-p-tolyl-4(3H)-quinazolinone(IVK)

Preparation required 2.50 g (10 mmol) of 2-methyl-3-p-tolyl-4(3H)-quinazolinone and 1.66 g (11 mmol) of ethyl nicotinate. After a reaction period of 4 hours, and using workup Method A, the yellow crude product was recrystallized from chloroform-isopropanol to give 2.87 g (81%) of yellow crystals, mp 267°–268°: $^1$H NMR (CDCl$_3$) δ 15.32 (broad s, 1H, enol), 8.64–7.05 (m, 12H, aromatic), 5.14 (s, 1H, vinyl) and 2.48 ppm (s, 3H, CH$_3$); ir (KBr) 1680 cm$^{-1}$ (C=O).

Anal. Calcd for C$_{22}$H$_{17}$N$_3$O$_2$: C, 74.35; H, 4.82; N, 11.82. Found : C, 74.27; H, 4.59; N, 11.71.

L.    2-[2-Oxo-2-(4 pyridyl)ethyl]-3-p-tolyl-4(3H)-quinazolinone(IVl)

Reaction of 2.50 g (10 mmol) of 2-methyl-3-p-tolyl-4(3H)-quinazolinone and 1.66 g (11 mmol) of ethyl isonicotinate for a period of 3 hours, followed by workup Method B, afforded a yellow solid which was recrystallized from dimethyl sulfoxide to give 3.0 g (84%) of product. An analytical sample was prepared by one recrystallization from dimethyl sulfoxide-chloroform. The resulting yellow microcrystals had mp 262°–263°: $^1$H NMR (DMSO-d$_6$ at 90°) δ 15.1 (very broad s, 1H, enol), 8.44–6.80 (m, 12H, aromatic), 5.05 (s, 1H, vinyl) and 2.40 ppm (s, CH$_3$). The methyl signal at δ 2.40 could not be integrated owing to the presence of an impurity in the DMSO-d$_6$; ir (KBr) 1680 cm$^{-1}$ (C=O).

Anal. Calcd for C$_{22}$H$_{17}$N$_3$O$_2$: C, 74.35; H, 4.82; N, 11.82. Found: C, 74.01; H, 4.47; N, 12.07.

M.    2-(3,3,3-Trifluoroacetonyl)-3-p-bromophenyl-4(3H)-quinazolinone (IVm)

Treatment of 3.15 g (10 mmol) of 2-methyl-3-p-bromophenyl-4(3H)-quinazolinone and 1.7 g (12 mmol) of ethyl trifluoroacetate with 1.2 g (25 mmol) of sodium hydride for a reaction period of 2 hours, followed by workup Method A, afforded a pink solid. The solid was recrystallized from chloroform-hexane to give 3.44 g (84%) of off-white crystals, mp 238°–239°: $^1$H NMR (CDCl$_3$) δ 14.53 (broad s, 1H, enol), 8.24–7.14 (m, 8H, aromatic) and 4.86 ppm (s, 1H, vinyl); ir (KBr) 1700 cm$^{-1}$ (C=O).

Anal. Calcd for C$_{17}$H$_{10}$BrF$_3$N$_2$O$_2$: C, 49.66; H, 2.45; N, 6.81. Found: C, 49.87; H, 2.27; N, 6.76.

N.    2-[2-Oxo-2-(2-pyridyl)ethyl]-3-p-bromophenyl-4(3H)-quinazolinone (IVn)

Treatment of 3.15 g (10 mmol) of 2-methyl-3-p-bromophenyl-4(3H)-quinazolinone and 1.81 g (12 mmol) of ethyl picolinate with 1.92 g (40 mmol) of sodium hydride (50%) in 160 ml of THF for a reaction period of 2.5 hours resulted in a yellow-brown reaction slurry which was processed using Method B. The crude yellow product was recrystallized from dimethyl sulfoxide-acetone to yield 4.06 g (96%) of yellow microcrystals, mp 312°–313° (dec): $^1$H NMR (CDCl$_3$ with 3 drops CF$_3$CO$_2$H) δ 8.96–7.11 (m, 12H, aromatic) and 5.50 ppm (s, 1H, vinyl); ir (KBr) 1685 cm$^{-1}$ C=O).

Anal. Calcd for C$_{21}$H$_{14}$BrN$_3$O$_2$: C, 60.62; H, 3.36; N, 10.00. Found: C, 60.18; H, 3.40; N, 9.75.

O.    2-[2-Oxo-2-(3-pyridyl)ethyl]-3-p-bromophenyl-4(3H)-quinazolinone(IVo)

The reaction of 2.0 g (6.3 mmol) of 2-methyl-3-p-bromophenyl-4(3H)-quinazolinone and 1.2 g (8 mmol) of ethyl nicotinate with 0.8 g (17 mmol) of 50% sodium hydride was carried out for a period of 2 hours. After using workup Method A, the crude product was recrystallized from isopropanol-chloroform-hexane to give 2.43 g (92%) of a yellow solid, mp 269°–270°; $^1$H NMR (CDCl$_3$) δ 15.50 (broad s, 1H, enol), 8.88–7.20 (m, 12H, aromatic) and 5.14 ppm (s, 1H, vinyl); ir (KBr) 1680 cm$^{-1}$ (C=O).

Anal. Calcd for C$_{21}$H$_{14}$BrN$_3$O$_2$: C, 60.02; H, 3.36; N, 10.00. Found: C, 60.20; H, 3.59; N, 9.85.

P.    2-[2-Oxo-2-(4-pyridyl)ethyl]-3-p-bromophenyl-4(3H)-quinazolinone (IVp)

This preparation employed 3.15 g (10 mmol) of 2-methyl-3-p-bromophenyl-4(3H)-quinazolinone and 1.81 g (12 mmol) of ethyl isonicotinate in the presence of 1.92 g (40 mmol) of sodium hydride in 160 ml of THF. After a reaction period of 2.5 hours, followed by workup Method B, a yellow solid was recrystallized from dimethyl sulfoxide to give 3.8 g (90%) of product. An analytical sample was prepared by recrystallization from chloroform-dimethyl sulfoxide. The resulting yellow microcrystals had a mp 307°–308° (dec): $^1$H NMR (CDCl$_3$ with 3 drops of CF$_3$CO$_2$H) δ 8.96–7.02 (m, 12H, aromatic) and 5.35 ppm (s, 1H, vinyl).

Anal. Calcd for C$_{21}$H$_{14}$BrN$_3$O$_2$: C, 60.02; H, 3.36; N, 10.00. Found: C, 59.73; H, 3.57; N, 9.68.

Q.    2-Acetonyl-3-p-bromophenyl-4(3H)-quinazaolinone (IVq)

To a refluxing slurry of 1.5 g (31 mmol) of 50% sodium hydride in 140 ml of THF was added 2.0 g (6.3 mmol) of 2-methyl-3-p-bromophenyl-4(3H)-quinazolinone and 0.88 g (10 mmol) of ethyl acetate in 15 ml of dry THF. After a reaction period of 3 hours, the reaction mixture was processed by using workup Method A. TLC analysis of the concentrate showed the presence of 2-methyl-3-p-bromophenyl-4(3H)-quinazolinone, the title product and ethyl acetacetate. Trituration of the concentrate with ether gave a solid, which was recrystallized from isopropanol-chloroform to afford 1.72 g (48%) of product as a yellow solid, mp 217°–219°: $^1$H NMR (CDCl$_3$) δ 15.07 (broad s, 1H, enol) 8.18 (d, J=8 Hz, 1H, 5-H), 7.86–7.14 (m, 7H, aromatic), 4.49 (s, 1H, vinyl) and 2.04 ppm (s, 3H, CH$_3$); ir (KBr) 1685 cm$^{-1}$ (C=O).

Anal. Calcd for C$_{17}$H$_{13}$BrN$_2$O$_2$: C, 57.16; H, 3.67; N, 7.84. Found: C, 57.05; H, 3.80; N, 7.99.

R.    2-(2-Oxo-2-phenylethyl)-3-methyl-4(3H)-quinazolinone (IVr)

1.20 g (25 mmol) of sodium hydride, as a 50% mineral oil dispersion, 0.87 g (5 mmol) of 2,3 dimethyl-4(3H)-quinazolinone and 0.75 g (5.5 mmol) of methyl benzoate were used. After a reaction period of 9.5 hours, and using workup Method A, the crude product was recrystallized from isopropanol-chloroform to yield 1.07 g (77%) of white crystals, mp 175°; $^1$H NMR (CDCl$_3$) δ (15.44 broad s, 1H, enol), 8.14 (d, J=8 Hz, 1H, 5-H), 8.00–7.13 (m, 8H, aromatic), 5.91 (s, 1H, vinyl) and 3.53 ppm (s, 3H, CH$_3$); ir (KBr) 1670 cm$^{-1}$ (C=O).

Anal. Calcd for C$_{17}$H$_{14}$N$_2$O$_2$: C, 73.37; H, 5.07; N, 10.07. Found: C, 73.22; H, 5.19; N, 9.74.

S.    2-[2-Oxo-2-(3-pyridyl)ethyl]-3-methyl-4(3H)-quinazolindone (IVs)

In this preparation, 2.6 g (54 mmols) of sodium hydride as a 50% mineral oil dispersion, 1.81 g (12 mmol) of ethyl nicotinate and 1.74 g (10 mmol) of 2,3 dimethyl-4-(3H)-quinazolinone were employed. After a reaction period of 2.5-3 hours, following workup Method A, the crude product was recrystallized from chloroform-hexane to yield two crops of yellow, amorphous solid for a total of 1.73 g (62%) of product. An analytical sample was prepared by recrystallization from chloroform, which produced yellow microcrystals, mp 244°-245° (dec); $^1$H NMR (CDCl$_3$-DMSO-d$_6$ with 2 drops of CF$_3$CO$_2$H) $\delta$ 9.34 (broad s, 1H, aromatic), 9.06-8.74 (m, 2H, aromatic), 8.18-7.20 (m, 5H, aromatic), 5.99 (s, 1H, vinyl) and 3.58 ppm (s, 3H, CH$_3$).

Anal. Calcd for C$_{16}$H$_{13}$N$_3$O$_2$: C, 68.81; H, 4.69; N, 15.04. Found: C, 68.78; H, 4.46; N, 15.32.

EXAMPLE 10

Evolution of Hydrogen Resulting from the Acylation of Methaqualone with Ethyl Trifluoroacetate at Room Temperature In the Presence of Excess NaH To a stirred solution of 1.0 g (7 mmol) of ethyl trifluoroacetate and 1.05 g (25 mmol) of sodium hydride (57%) in 130 ml of dry DME at 26° was added 1.25 g (5 mmol) of methaqualone in 20 ml of DME. After 1.5 hours, 186 ml (8.3 mmol) of hydrogen at STP was evolved from the gray reaction slurry. After a total reaction period of 2.5 hours, no additional hydrogen was generated. TLC analysis (ether) of a reaction mixture aliquot quenched with acetic acid revealed the presence of 2-(3,3,3-trifluoroacetonyl)-3-o-tolyl-4(3H)-quinazolinone and methaqualone. The reaction was brought to reflux and the reaction was allowed to continue for 1 more hour. The resulting mixture was worked up as described for the preparation of 2-(3,3,3-trifluoroacetonyl)-3-o-tolyl-4(3H)-quinazolinone to afford 1.4 g (81%) of product IIIa, mp 193°-194°. The $^1$H NMR spectrum of this material was identical with that of 2-(3,3,3-trifluoroacetonyl)-3-o-tolyl-4(3H)-quinazolinone.

When the experiment described above was repeated in the absence of ethyl trifluoroacetate, no hydrogen was evolved. In order to investigate the reason for the apparently increased acidity of methaqualone in the presence of ethyl trifluoroacetate, uv and $^1$H NMR studies were carried out to detect a possible complex between the ester and methaqualone. A comparison of the uv spectrum of an equimolor solution (5×10$^{-4}$ M) of methaqualone and ethyltrifluoroacetate and the spectra of individual compounds at the same concentrations (5×10$^{-4}$ M) revealed them to be essentially identical with regard to peak shape and wavelength of absorption.

The chemical shift differences (0.07-0.08 ppm) of the $^1$H NMR signals arising from the 2-methyl group and the o-tolyl methyl substituent of methaqualone in CDCl$_3$ remained essentially unchanged regardless of the amount of ethyl trifluoroacetate present. The chemical shift difference of the same methyl groups of methaqualone was 0.31 ppm when 2 drops of trifluoroacetic acid was added to a CDCl$_3$ solution of methaqualone. The $^{19}$F NMR signal of the trifluoromethyl group of ethyl trifluoroacetate was unsatisfactory for monitoring possible interaction between the ester and methaqualone since the fluorine resonance of the ester showed solvent (CDCl$_3$) dependency.

EXAMPLE 11

PHARMACOLOGICAL TESTING OF NEW 2,3-DISUBSTITUTED-4(3H)-QUINAZOLINONES

Representative compounds according to the present invention were tested for central nervous system activity by Pharmakon Laboratories of Scranton, Pennsylvania. The battery of general observational procedures used is referred to herein as a Neuropharmacological Profile (NPP). Additionally, representative compounds were tested in the Anticonvulsant Screening Project of the National Institutes of Neurological and Communicative Disorders and Stroke (NINCDS) at the University of Utah under the direction of Dr. Ewart A. Swinyard.

A. Neuropharmacological Profile (NPP)

The procedures for the determination of a neuropharmacological profile involved white male mice of the Carworth Farm Strain CF-1 weighing 18 to 22 grams. The test compound, regardless of solubility, was suspended in a 0.25% aqueous methylcellulose solution. Intraperitoneal injections were administered in logarithmic progression and sequentially. The dose levels employed routinely were 10, 30, 100 and 300 mg/kg, using four male mice at each dose level. Since this test was conducted in a sequential manner, the first does administered was at 300 mg/kg. The mice were injected at this dose level and observed for gross changes produced by the drug, e.g. as behavioral, neurological, autonomic and toxic effects. Approximately thirty-eight signs and symptoms of pharmacological activity can be identified.

The animals were observed continuously for one hour and, if no signs of pharmacological or toxicological activity were present at the end of the first hour, they were intermittently checked for activity every fifteen minutes thereafter for two consecutive hours. At the end of the third hour of observation, if no demonstrable change had occurred in the behavior of the mice, the compound was conditionally considered inactive and the animals were checked intermittently for forty-eight hours. Subsequent does levels below 300 mg/kg were not administered in this case. Alternatively, if demonstrable pharmacological changes occurred within the first three hours after administration of the drug at 300 mg/kg, the subsequent doses were administered and the animals were observed for changes in overt behavior. The observation period began immediately following the injection and the animals were then continuously observed for three hours and intermittently checked thereafter for forty-eight hours. The animals were observed and signs and symptoms of pharmacological activity were recorded continuously until no further symptoms developed and until the symptoms that appeared were no longer present. In certain instances, such as with reserpine, the effects of a single dose can exceed the forty-eight hour observation period. In such instances, the animals were observed beyond this period until they returned to normal. Routinely, the number of animals alive at the end of the forty-eight hour observation period was recorded and the LD$_{50}$ estimated.

The animals were observed in a fixed environment consisting of a 15" square in which their movement was not restricted. They were placed on an absorbent paper which detects excretions, especially increased urination, which may indicate diuretic activity. The animals are free to move about for evaluation of spatial orientation, alertness and spontaneous motor activity. The animals were systematically observed and manipulated to measure the onset, peak effect, duration and character of drug action.

Since this is a general CNS screening procedure, only peak effects were recorded. Certain measures of behavior and neurological deficit were scored in terms of intensity of effect, while most others were determined on an all or none basis. Thus, in scoring measures which were normally present, e.g., spontaneous activity and skin color, an increase in score from 4 to 8 was used to denote stimulation or enhancement of skin color, whereas a decrease in score from 4 to 0 indicated depression or cyanosis. For scoring measures normally absent, e.g., depression, righting reflex and ataxia, activity was reflected as an increase in score from 0 to 8. The 0 to 8 scale was rounded off so that the actual ratings are only 0, 2, 4, 6 and 8. The compounds were also evaluated for anticonvulsant activity by using the maximal electroshock seizure (MES) test. In the MES study, four mice were dosed intraperitoneally at 100 mg/kg and challenged thirty minutes later with 50 mA, 0.2 second duration of electroshock. A protection ratio (number of mice protected from tonic extension ÷ number of mice tested) was then established.

At the termination of the test, the results were recorded and tabulated. Based on the symptom complex observed and the score values, a suggested pharmacological activity was indicated.

B. NINCDS Identification of Anticonvulsant Activity

1. Neurological Activity Tests. The biological testing program is designed to evaluate the following four aspects of drug action: (1) the existence and specificity of anticonvulsant activity; (2) the toxicity, particularly to the central nervous system; and, if the results of (1) and (2) are favorable, (3) the potency and protective index, a comparison between toxic and effective dose and (4) the time course of activity. Compounds were evaluated for anticonvulsant activity in two seizure models, the maximal electroshock seizure (MES) test and the subcutaneous pentylenetetrazol (Metrazol) seizure threshold (scMet) test.

The Maximal Electroshock Seizure Test was performed according to the method described by Swinyard and coworkers,* wherein a drop of 0.9% saline is instilled in each eye prior to application of corneal electrodes. Seizures are elicited with a 50 Hz alternating current of 50 mA (5 to 7 times that necessary to elicit minimal electroshock seizures) delivered for 0.2 sec via corneal electrodes. This stimulus will produce a maximal seizure in all normal mice. The maximal seizure typically consists of a short period of initial tonic flexion and a prolonged period of hind limb tonic extension, followed by terminal clonus. The seizure lasts about 22 seconds. Abolition of the hind limb tonic extensor component of the seizure is defined as protection and indicates anticonvulsant activity in the test compound.
*Epilepsia 10 : 107 (1969)

Subcutaneous Pentylenetetrazol (Metrazol) Seizure Threshold Test (scMet) produces threshold (clonic) seizures. Pentylenetetrazol is administered subcutaneously as a threshold 0.5% solution (in 0.9% sodium chloride) in a loose fold of skin on the back of the neck in a dose of 85 mg/kg. Seizures are produced in at least 97% of the mice. Metrazol is given 10 minutes before the beginning of the test to allow for the delay in onset of Metrazol action. The animal is observed for 30 minutes. Failure to observe even a threshold seizure (a single episode of clonic spasms at least 5 seconds in duration) is defined as protection and indicates anticonvulsant activity in the test compound. These two methods of seizure provocation reliably elicit well-characterizied seizure phenomena. Together, they have been shown sufficient to identify all compounds known to demonostrate anticonvulsant activity in other tests.

The ability of a compound to prevent maximal electroshock seizures is believed to correlate with its ability to prevent the spread of seizure discharge through neural tissue. Activity against maximal electroshock seizures is thought to indicate potential efficacy in the treatment of major motor (grand mal) seizures. Phenytoin, or 5,5-diphenyl-2,4-imidazolidinedione, is the antiepileptic drug best known for its selective action is preventing maximal seizures. The ability of a compound to prevent threshold seizures induced by subcutaneous pentylenetetrazol has been correlated with the ability to raise the threshold for excitation of neutral tissue. Selective action in the test is believed to indicate potential efficacy against absence (petit mal) seizures. The benzodiazepines, e.g. diazepam, are the most potent drugs known to act selectively in preventing Metrazol-induced threshold seizures.

Central nervous system toxicity was evaluated in the rotorod ataxia test. This test is designed to detect minimal neurotoxicity. The animal is placed on a 1-inch diameter knurled plastic rod rotating at 6 rpm. Normal mice can remain indefinitely on a rod rotating at this speed. Neurological deficit is defined as the failure of the animal to remain on the rod for at least 1 minute. This test has a clear end-point, is quantifiable and correlates well with the clinical assessment of minimal toxicity.

C. Results of the Neuropharmacological Profiles

The results of the Pharmakon Neuropharmacological Profiles of twenty new compounds along with the profiles of methaqualone and the 2-methyl-4(3H)-quinazolinones 67 and 37 are reported in Tables I and II. Table I contains results of compounds prepared from methaqualone, while Table II presents the findings for other 4(3H)-quinazolinones which contain 3-substituents other than an o-tolyl group. Scores for behavioral symptoms, including depression, righting reflex and ataxia, are the actual numbers reported. Protection against MES is reported as a percentage. Since four animals were involved in this test, the findings are 0% for none protected, 25% for one out of four, etc. An $LD_{50}$ of 562 or greater means that no deaths occurred during the observation period. In order to maintain reasonable uniformity in the reporting of results, each entry corresponds to a dosage level of 100 mg/kg. Any variations from that dosage are indicated.

Table I

NPP Results for 2-Substituted-3-o-tolyl-4(3H)-quinazolinones

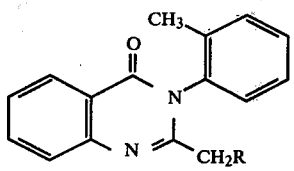

| Compound Number | R | CNS Depression at 100 mg/kg and (30 mg/kg) | % MES Protection at 100 mg/kg | $LD_{50}$ mg/kg |
| --- | --- | --- | --- | --- |
|  | H (methaqualone) | $(8)^{a,b,c}$ | $0^d$ | >562 |
| IIIg | $COC_6H_5$ | 4(4) | 0 | >562 |
| IIIh | $COC_6H_4Cl$-p | $0^e$ | 0 | 316 |
| IIIj | $COC_6H_2(OCH_3)_3$-3,4,5 | $2^e$ | 0 | >562 |
| IIIi | $COC_6H_4OCH_3$-p | $2^e$ | 0 | >562 |
| IIIm | $COCO_2C_2H_5$ | 4 | 0 | >562 |
| IIIf | $COCH=CHC_6H_5$ | 4(2) | 25 | >562 |
| IIIa | $COCF_3$ | $(4)^{c,f}$ | 50 | >562 |
| IIIn | $COCH_3$ | 8(4) | 0 | >562 |
| IIIb | CO-2-pyridyl | 2 | 0 | >562 |
| IIIc | CO-3-pyridyl | $6(4)^b$ | 100 | 562 |
| IIId | CO-4-pyridyl | $0^e$ | 0 | >562 |

[a] Righting Reflex = 8 at 100 mg/kg.
[b] Ataxia = 8 at 100 mg/kg.
[c] Depression not determined at 100 mg/kg.
[d] MES protection at 30 mg/kg.
[e] Depression = 4 at 300 mg/kg.
[f] Ataxia = 2 at 100 mg/kg.

Table II

NPP Results for 2,3-Disubstituted-4(3H)-quinazolinones

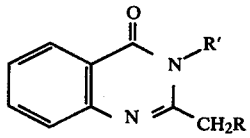

| Compound Number | R' | R | CNS Depression at 100 mg/kg and (30mg/kg) | % MES Protection at 100 mg/kg | $LD_{50}$ mg/kg |
| --- | --- | --- | --- | --- | --- |
| IVa | o-chlorophenyl | $COCF_3$ | 8(6) | $0^a$ | 178 |
| IVb | o-chlorophenyl | CO-2-pyridyl | $0^b$ | 0 | 562 |
| IVc | o-chlorophenyl | CO-3-pyridyl | 4 | 25 | 562 |
| IVd | o-chlorophenyl | CO-4-pyridyl | $6(2)^{c,d,e}$ | $50^a$ | 237 |
|  | p-tolyl | H | $8(4)^f$ | 100 | >562 |
| IVi | p-tolyl | $COCF_3$ | $4^g$ | 100 | 562 |
| IVk | p-tolyl | CO-3-pyridyl | 4 | 0 | 562 |
|  | phenyl | H | $8(4)^{c,f}$ | $0^a$ | 562 |
| IVe | phenyl | $COCF_3$ | 2 | 0 | 562 |
| IVg | phenyl | CO-3-pyridyl | 2 | 0 | 562 |
| IVs | $CH_3$ | CO-3-pyridyl | 4 | 0 | 422 |

[a] Conducted at 30 mg/kg
[b] Depression = 2 at 300 mg/kg.
[c] Righting reflex = 8 at 100 mg/kg.
[d] Ataxia = 6 at 100 mg/kg.
[e] Depression = 2 at 10 mg/kg.
[f] Ataxis = 8 at 100 mg/kg.
[g] Ataxia = 2 at 100 mg/kg.

D. NINCDS Primary Evaluation Results

Specific anticonvulsant evaluations performed by NINCDS using MES, scMet and Rotorod assays are presented in Tables III & IV for fourteen new compounds as well as several known compounds. Table III centers attention on 2-substituted-3-o-tolyl-4-(3H)-quinazolinones while Table IV includes the findings for various other 2,3-disubstituted-4(3H)-quinazolinones. As described earlier, the MES, scMet and Rotorod tests were performed one-half hour and four hours after administration of each compound. The tables identify the dosage level that elicited a positive result, such as protection against MES and scMet induced seizures, or loss of balance on the rotorod. Compounds which did not exhibit activity in any of the 3 categories at dose levels of 300 mg/kg were placed in Class III by NINCDS and are not listed.

The anticonvulsant activity and neurotoxicity of the model compounds methaqualone (3) and mecloqualone (4a) are apparent from the results presented in Tables III and IV Mecloqualone is more effective in protection against scMet induced seizures, while methaqualone is more active in the MES test. This illustrates the need for having two tests that apparently are selective for convulsive seizures which are aroused by different physiological mechanisms.

(4) that the behavioral activity elicited by the derivative of mecloqualone where R=CO-4-pyridyl ap-

Table III

Results of Primary Evaluation of 2-Substituted-3-o-tolyl-4(3H)-quinazolinones in the NINCDS Anticonvulsant Screening Project

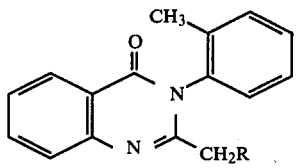

| Compound Number | R | MES, mg/kg after 0.5 hr or (4 hr) | | scMet, mg/kg after 0.5 hr or (4 hr) | | Rotorod mg/kg after 0.5 hr or (4 hr) | | NINCDS Classification |
|---|---|---|---|---|---|---|---|---|
| | H (methaqualone) | 100 | (300) | 100 | (300) | 100 | (300) | II |
| | CHOHC$_6$H$_5$ | | | 300 | | | (300) | II |
| | CH$_3$ | 100 | (300) | 100 | (300) | 100 | (300) | II |
| IIIn | COCH$_3$ | | | | (300) | | | II |
| IIIb | CO-2-pyridyl | | | 300 | | | | II |
| IIIc | CO-3-pyridyl | | | | (300) | | | II |
| IIId | CO-4-pyridyl | 100 | | 30 | (300) | | | I |
| IIIe | COC$_6$H$_4$—NHCOCF$_3$-$p$ | | | 300 | | 300 | | II |
| | CH$_2$C$_6$H$_5$ | | | 300 | (300) | | | II |
| | CO-3-C$_5$H$_4$N$^+$CH$_3$I$^-$ | | (100) | | (30) | 100 | | I$^a$ |
| | H and 7-amino | 100 | (100) | 100 | (100) | 100 | (300) | II$^a$ |

$^a$Extremely toxic

Table IV

Results of Primary Evaluation of 2,3-Disubstituted-4(3H)-quinazolinones in the NINCDS Anticonvulsant Screening Project

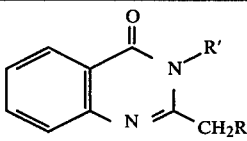

| Compound No. | R' | R | MES, mg/kg after 0.5 hr or (4 hr) | | scMet, mg/kg after 0.5 hr or (4 hr) | | Rotorod, mg/kg after 0.5 hr or (4 hr) | | NINCDS Classification |
|---|---|---|---|---|---|---|---|---|---|
| | o-chlorophenyl | H (mecloqualone) | | (300) | 30 | (100) | 30 | (100) | I$^a$ |
| IVa | o-chlorophenyl | COCF$_3$ | | | | | 300 | (300) | III |
| IVc | o-chlorophenyl | CO-3-pyridyl | | | 300 | (300) | | (300) | II |
| IVd | o-chlorophenyl | CO-4-pyridyl | 300 | (100) | 30 | (100) | | | I |
| IVl | p-tolyl | CO-4-pyridyl | | | | (300) | | | II |
| IVg | phenyl | CO-3-pyridyl | 100 | | 100 | | | | I |
| IVh | phenyl | CO-4-pyridyl | | | 100 | | | | II |
| IVr | methyl | COC$_6$H$_5$ | | | | | | (300) | II |

$^a$Extremely toxic

In the present series, the majority of activity observed was in the scMet test. Positive scMet results were elicited by thirteen of the new compounds, of which only four gave indications of MES protection; all four had an R group which contained a 3-pyridyl or 4-pyridyl substituent.

In summary, the results of the Neuropharmacological Profiles indicated:

(1) that depression was exhibited by eighteen of twenty new compounds at 100 mg/kg or less;

(2) that 2,3-disubstituted quinazolinones with R=COCH$_3$, COCF$_3$, CO-3-pyridyl and CO-4-pyridyl cause depression and, in most instances, ataxia and loss of righting reflex if the 3-aryl grouping is ortho-substituted with either a chloro or methyl moiety;

(3) that the derivative of methaqualone where R=COCH$_3$ is equal to methaqualone in affecting behavioral activity and displayed possible muscle relaxant properties not exhibited by methaqualone itself; and proaches that of methaqualone.

The results of the Primary Anticonvulsant Evaluation showed:

(1) that of twenty-nine new compounds submitted, thirteen displayed anticonvulsant activity;

(2) that the anticonvulsant activity of these thirteen compounds was most prominent in the area of scMet protection, but four also gave positive results in the MES test;

(3) a structure-activity correlation in which scMet activity was associated with R=CO-4-pyridyl and a 3-aryl group containing either an ortho methyl or ortho chloro substituent; and (4) a lack of neurotoxicity of each of the above.

E. NINCDS Secondary Evaluation Results

Owing to their promising activity in the NINCDS Primary Evaluation, 2-[2-oxo-2-(4-pyridyl)ethyl]-3-o-tolyl-4(3H)-quinazolinone (IIId) and 2-[2-oxo-2-(4-pyridyl) ethyl]-3-o-chlorophenyl-4(3H)quinazolinone (IVd)

were subjected to Secondary Evaluation along with methaqualone as a standard for comparison. In the Secondary Evaluation, median effective doses (ED$_{50}$) are determined in the MES, scMet and Rotorod assays using the procedures defined in Pharmacology, 95, 99–113 (1949). In addition, each compound's anticonvulsant activity and neurotoxicity over time are determined by measuring the effect of an intraperitoneally administered estimated median effective dose on maximal electroshock seizures and rotorod performance at intervals of ½, 1, 2, 3, 4, 6 and 8 hours.

TABLE V

Secondary Evaluation of Selected 2-Substituted-3-aryl-4(3H) quinazolinones in the NINCDS Anticonvulsant Screening Project

| Compound No. | MES ED$_{50}$, mg/kg | scMet ED$_{50}$, mg/kg | Rotorod TD$_{50}$, mg/kg | PI* MES | scMet |
|---|---|---|---|---|---|
| methaqualone | 52 | 33.5 | 55 | 1.05 | 1.64 |
| IIId | 74 | 75 | 440 | 5.94 | 5.86 |
| IVd | 33.5 | 30.8 | 137 | 4.08 | 4.44 |

*PI = Protective Index = TD$_{50}$/ED$_{50}$

Separate groups of animals are used for each time period. The times of peak toxic and anticonvulsant effect are taken from the resulting graph of percent of animals responding vs. time, and the determinations of median effective doses are performed at those times. The results o these assays are presented in Table V.

The results of the Secondary Anticonvulsant Evaluation show:

(1) that IVd is more potent against scMet and electroshock-induced seizures than methaqualone;

(2) that IVd has an approximately four-fold higher protective index in both scMet and MES assays than methaqualone;

(3) that IIId is less potent than methaqualone in both scMet and MES tests;

(4) that IIId has an approximately five-fold higher protective index than methaqualone in both scMet and MES tests;

(5) that IVd has a lower ED$_{50}$ in the scMet screen than the commercially available petit mal agents Ethotoin, Trimethadione, Paramethadione, Ethosuximide, Methsuximide, Phensuximide and Phenacamide when compared to similar data for these compounds reported in DHEW Publication No. (NIH) 76-1093;

(6) that IVd has a higher scMet protective index than Ethosuximide; and (7) that IVd has a higher MES protective index than Ethotoin, Mephenytoin, Phenobarbital, Metharbital, Trimethadione, Paramethadione, Methsuximide, Phensuximide, Diazepam and Clonazepam.

EXAMPLE 12

Using the sodium hydride method described in Example 2, the following additional compounds of Formula IV were prepared:

| IV t R$_3$ = o-bromopenyl; | R$_5$ = 4-pyridyl |
| IV u R$_3$ = o-fluorophenyl; | R$_5$ = 4-pyridyl |
| IV v R$_3$ = o-methoxyphenyl; | R$_5$ = 4-pyridyl |
| IV w R$_3$ = 2,6-dichlorophenyl; | R$_5$ = 4-pyridyl |
| IV x R$_3$ = m-chlorophenyl; | R$_5$ = 4-pyridyl |

$^1$HNMR spectrum are in good agreement with the proposed structure.

The preceding examples can be repeated with similar success by substituting the generically or specifically described components and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for inducing hypnotic sedation in a living mammal, which comprises administering to said mammal a safe and sedative-hypnotic amount of a 2-ketoalkyl-4(3H)-quinazolinone having sedative-hypnotic activity of the formula

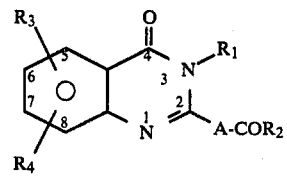

wherein
A is divalent alkylene of 1–10 carbon atoms;
R$_1$ is alkyl of 1–3 carbon atoms, alkylphenyl of 1–3 carbon atoms in the alkyl substituent, halophenyl or dihalophenyl;
R$_2$ is alkyl of 1–3 carbon atoms, alkenyl of 2–5 carbon atoms or pyridyl; and
at least one of R$_3$ and R$_4$ is hydrogen and the other is hydrogen, hydroxy, amino, halogen, trifluoromethyl, alkyl, alkoxy, alkylthio or alkylsulfonyl each of 1–4 carbon atoms.

2. A process for preventing convulsions in a living mammal which comprises administering to said mammal a safe and anti-convulsant amount of a 2-ketoalkyl-4(3H)-quinazolinone having anticonvulsant activity of the formula

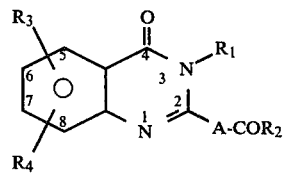

wherein
A is divalent alkylene of 1–10 carbon atoms;
R$_1$ is alkyl of 1–3 carbon atoms, alkylphenyl of 1–3 carbon atoms in the alkyl substituent, halophenyl or dihalophenyl;
R$_2$ is alkyl of 1–3 carbon atoms, alkenyl of 2–5 carbon atoms or pyridyl; and
at least one of R$_3$ and R$_4$ is hydrogen and the other is hydrogen, hydroxy, amino, halogen, trifluoromethyl, alkyl, alkoxy, alkylthio or alkylsulfonyl each of 1–4 carbon atoms.

3. A process according to claim 2, wherein said anticonvulsant amount is less than a sedative-hypnotic amount of said compound.

4. A pharmaceutical composition comprising a pharmaceutically acceptable carrier in combination with a safe and CNS depressant amount of a 2-ketoalkyl-4(3H)-quinazolinone having sedative-hypnotic and/or anticonvulsant activity of the formula:

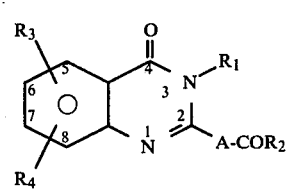

wherein
  A is divalent alkylene of 1–10 carbon atoms;
  $R_1$ is alkyl of 1–3 carbon atoms, alkylphenyl of 1–3 carbon atoms in the alkyl substituent, halophenyl or dihalophenyl;
  $R_2$ is alkyl of 1–3 carbon atoms, alkenyl of 2–5 carbon atoms or pyridyl; and
  at least one of $R_3$ and $R_4$ is hydrogen and the other is hydrogen, hydroxy, amino, halogen, trifluoromethyl, alkyl, alkoxy, alkylthio or alkylsulfonyl each of 1–4 carbon atoms.

5. A composition according to claim 4, wherein said quinazolinone compound is present in a sedative-hypnotic amount.

6. A composition according to claim 4, wherein said quinazolinone compound is present in an anti-convulsant amount.

7. A composition according to claim 6, wherein said anti-convulsant amount is less than a sedative-hypnotic amount.

8. A 2-ketoalkyl-4(3H)-quinazolinone having sedative-hypnotic and/or anticonvulsant activity of the formula

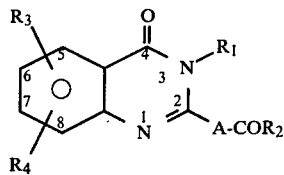

wherein
  A is divalent alkylene of 1–3 carbon atoms;
  $R_1$ is alkylphenyl of 1–3 carbon atoms in the alkyl substituent, halophenyl or dihalophenyl;
  $R_2$ is alkyl of 1–3 carbon atoms, alkenyl of 2–5 carbon atoms or pyridyl; and
  at least one of $R_3$ and $R_4$ is hydrogen and the other is hydrogen, hydroxy, amino, halogen, trifluoromethyl, alkyl, alkoxy, alkylthio or alkylsulfonyl each of 1–4 carbon atoms.

9. A compound according to claim 8, wherein A is methylene.

10. A compound according to claim 8, wherein $R_1$ is alkyphenyl of 1–3 carbon atoms in the alkyl substituent.

11. A compound according to claim 8, wherein $R_1$ is o-tolyl or p-tolyl.

12. A compound according to claim 11, wherein $R_2$ is pyridyl.

13. A compound according to claim 12, 2-[2-Oxo-2-(4-pyridyl)ethyl]-3-o-tolyl-4(3H)quinazolinone.

14. A compound according to claim 8, wherein $R_1$ is halophenyl or dihalophenyl.

15. A compound according to claim 14, wherein $R_1$ is o- or p-chlorophenyl or o- or p-bromophenyl.

16. A compound according to claim 15, wherein $R_2$ is pyridyl.

17. A compound according to claim 16, 2-[2-Oxo-2-(4-pyridyl)ethyl]-3-o-chlorophenyl-4(3H)-quinazolinone.

* * * * *